United States Patent [19]

Takefuji et al.

[11] Patent Number: 5,763,463
[45] Date of Patent: Jun. 9, 1998

[54] PYRIDINE COMPOUNDS WHICH ARE USEFUL AS PESTICIDES

[75] Inventors: Nobuo Takefuji; Masao Nakatani; Junko Suzuki; Masami Ozaki; Ryouhei Ueno; Hiroyuki Yano; Mieko Kawashima, all of Shizuoka-ken; Yutaka Kurihara, Nagoya; Tomonori Shimazu, Hamamatsu, all of Japan

[73] Assignees: Kumiai Chemical Industry Co., Ltd.; Ihara Chemical Industry Co., Ltd., both of Tokyo, Japan

[21] Appl. No.: 849,718

[22] PCT Filed: Apr. 23, 1996

[86] PCT No.: PCT/JP96/01096

§ 371 Date: Jun. 25, 1997

§ 102(e) Date: Jun. 25, 1997

[87] PCT Pub. No.: WO96/33975

PCT Pub. Date: Oct. 31, 1996

[30] Foreign Application Priority Data

Apr. 28, 1995 [JP] Japan ................... 7-129086

[51] Int. Cl.⁶ ................ C07D 213/75; C07D 213/71; A01N 43/40
[52] U.S. Cl. ................ 514/352; 504/130; 546/309
[58] Field of Search ................ 504/130; 546/309; 514/352

[56] References Cited

U.S. PATENT DOCUMENTS 5,399,564  3/1995  Hackler et al. ................... 514/313

FOREIGN PATENT DOCUMENTS 5-221990   8/1993  Japan ................... 514/313
WO93/04580 3/1993  WIPO  ................... 514/313

*Primary Examiner*—Zinna Northington Davis
*Attorney, Agent, or Firm*—Oblon, Spivak, McClelland, Maier & Neustadt, P.C.

[57] ABSTRACT

A pyridine derivative of the formula (I), or its oxide or salt:

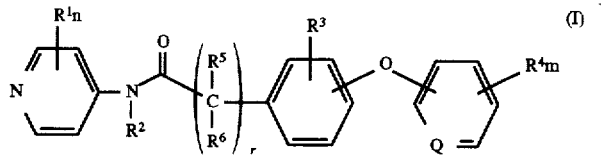

wherein $R^1$ is a halogen atom, an alkyl group, etc., $R^2$ is an alkenyl group, an alkynyl group, an alkoxycarbonyl group, an alkenyloxycarbonyl group, etc., $R^3$ is a hydrogen atom, etc., $R^4$ is a halogen atom, a cyano group, a haloalkyl group, etc., each of $R^5$ and $R^6$ is a hydrogen atom, etc., Q is a methine group or a nitrogen atom, m is 0 or 1, n is 1 or 2 and r is 1 or 2. Such a compound is useful as a pesticide. The compound of the present invention is a pyridine derivative which is capable of killing or controlling various pests without adversely affecting crop plants and which is readily decomposable and presents no substantial acute toxicity to mammals.

7 Claims, No Drawings

PYRIDINE COMPOUNDS WHICH ARE USEFUL AS PESTICIDES

This is a 371 application of PCT/JP96/01096 filed Apr. 23, 1996.

TECHNICAL FIELD

The present invention relates to a novel pyridine derivative and a pesticide containing it as an active ingredient.

BACKGROUND TECHNIQUE

Heretofore, a number of pesticidal compounds have been reported (Japanese Unexamined Patent Publications No. 221990/1993). However, the pyridine derivative of the present invention has not been known.

In recent years, it has been desired to develop a new pesticide which is highly effective at a low dose and which is highly safe.

The present inventors have synthesized various pyridine derivatives and have studied them to find compounds which have high pesticidal, activities and which are highly safe. As a result, it has been found that the compound of the present invention exhibits outstanding pesticidal activities against various pests, particularly against agricultural and horticultural pests including lepidopteran injurious insects represented by beat armyworm (*Spodoptera exigua*), diamond back (*Plutella xylostella*) and Asiatic rice borer (*Chio suppressalis*), and plant pathogens such as rice blast fungus (*Piricularia oryzae*), wheat powdery mildew fungus (*Erysiphe graminis*), leaf rust fungus (*Puccinia recondita*), cucumber downy mildew fungus (*Pseudoperonospora cubensis*) and apple scrab fungus (*Venturia inaequalis*). The present invention has been accomplished on the basis of this discovery.

DISCLOSURE OF INVENTION

That is, the present invention provides (1) a pyridine derivative of the formula (I) or its oxide or salt (I):

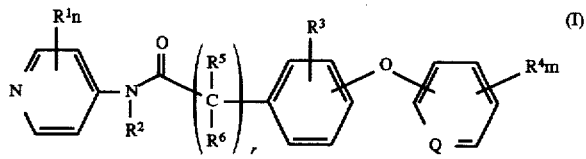

wherein $R^1$ is a halogen atom, a $C_{1-6}$ alkyl group, a $C_{1-6}$ haloalkyl group, a $C_{3-7}$ cycloalkyl group, a $C_{1-6}$ alkoxy group or a $C_{1-6}$ haloalkoxy group, provided that a plurality of $R^1$ may be the same or different, $R^2$ is a $C_{2-6}$ alkenyl group, a $C_{2-6}$ alkynyl group, an alkoxyalkyl group, an alkoxycarbonylalkyl group, a group of the formula —COOR$^7$ [wherein $R^7$ is a $C_{1-10}$ alkyl group, a $C_{1-10}$ haloalkyl group, a $C_{2-6}$ alkenyl group, a $C_{2-6}$ alkynyl group, a $C_{3-7}$ cycloalkyl group, a cycloalkylalkyl group, an alkoxyalkyl group, a phenyl group (which may be substituted by a halogen atom, a nitro group, a $C_{1-6}$ alkyl group, a $C_{1-6}$ haloalkyl group or a $C_{1-6}$ alkoxy group), or a benzyl group (which may be substituted by a halogen atom, a nitro group, a $C_{1-6}$ alkyl group, a $C_{1-6}$ haloalkyl group or a $C_{1-6}$ alkoxy group)] or a group of the formula —SNR$^9$R$^{10}$ (wherein R$^9$ is a $C_{1-6}$ alkyl group, an alkoxycarbonyl group or an alkoxycarbonylalkyl group, and R$^{10}$ is a $C_{1-6}$ alkyl group, an alkoxycarbonyl group or an alkoxycarbonylalkyl group, provided that R$^9$ and R$^{10}$ may be the same or different); $R^3$ is a hydrogen atom, a halogen atom, a $C_{1-6}$ alkyl group or a $C_{1-6}$ alkoxy group; $R^4$ is a halogen atom, a cyano group, a nitro group, a $C_{1-6}$ alkyl group, a $C_{1-6}$ haloalkyl group, a group of the formula —COOR$^8$ (wherein R$^8$ is a $C_{1-6}$ alkyl group, a benzyl group or an alkyl-substituted silylalkyl group), a $C_{1-6}$ alkylthio group, a $C_{1-6}$ alkylsulfinyl group, a $C_{1-6}$ alkylsulfonyl group, a $C_{1-6}$ haloalkoxy group or a $C_{1-6}$ haloalkylthio group, provided that a plurality of R$^4$ may be the same or different; each of R$^5$ and R$^6$ which may be the same or different, is a hydrogen atom or a $C_{1-6}$ alkyl group; Q is a methine group or a nitrogen atom; m is an integer of from 0 to 2; n is an integer of from 0 to 4; and r is an integer of from 1 to 4; and (2) a pesticide containing such a compound as an active ingredient.

Now, the terms used in this specification will be defined.

The oxide represents an N-oxide of the nitrogen atom of the pyridine ring of the compound of the formula (I).

The salt represents a salt of the compound of the formula (I) with a mineral acid such as hydrochloric acid, sulfuric acid or nitric acid or with an organic acid such as acetic acid, oxalic acid, citric acid or picric acid.

In the present invention, the halogen atom represents a fluorine atom, a chlorine atom, a bromine atom or an iodine atom.

The alkyl group means a linear or branched $C_{1-10}$ alkyl group such as a methyl group, an ethyl group, a n-propyl group, an isopropyl group, a n-butyl group, an isobutyl group, a sec-butyl group, a tert-butyl group, a n-pentyl group, an isoamyl group, a neopentyl group, a n-hexyl group, an isohexyl group, a 3,3-dimethylbutyl group, a n-heptyl group, a n-octyl group, a n-nonyl group or a n-decyl group, unless otherwise specified.

The haloalkyl group represents a linear or branched $C_{1-10}$ alkyl group which is substituted from 1 to 10 halogen atoms which may be the same or different, such as a trifluoromethyl group.

The cycloalkyl group represents a $C_{3-7}$ cycloalkyl group such as a cyclopropyl group, a cyclopentyl group or a cyclohexyl group.

The alkoxy group represents an alkyl-O- group wherein the alkyl moiety is as defined above, and it may, for example, be a methoxy group, an ethoxy group, a n-propoxy group, an isopropoxy group, a n-butoxy group, an isobutoxy group, a sec-butoxy group, a tert-butoxy group, a n-hexyloxy group or a n-octyloxy group.

The haloalkoxy group represents a haloalkyl-O- group wherein the haloalkyl moiety is as defined above, and it may, for example, be a trifluoromethoxy group or a 2,2,2-trifluoroethoxy group.

The alkenyl group represents a $C_{2-6}$ alkenyl group such as an ethenyl group or a 2-propenyl group.

The alkynyl group represents a $C_{2-6}$ alkynyl group such as an ethylnyl group or a propynyl group.

The alkoxyalkyl group represents an alkyl-O-alkyl group wherein each alkyl moiety is as defined above, and it may, for example, be a methoxymethyl group, a methoxyethyl group, an ethoxymethyl group or an ethoxyethyl group.

The alkoxycarbonylalkyl group represents an alkoxy-CO-alkyl group wherein the alkyl moiety and the alkoxy moiety are as defined above, and it may, for example, be a methoxycarbonylmethyl group.

The cycloalkylalkyl group, wherein the cycloalkyl moiety and the alkyl moiety are as defined above, may, for example, be a cyclopropylmethyl group or a cyclohexylethyl group.

The alkyl-substituted silylalkyl group, wherein each alkyl moiety is as defined above, may, for example, be a trimethylsilylmethyl group or a trimethylsilylethyl group.

Among compounds of the formula (I), preferred are compounds wherein $R^1$ is a chlorine atom and an ethyl group, $R^2$ is an alkoxyalkyl group, an alkoxycarbonylalkyl group, an alkenyl group, an alkynyl group, an alkoxycarbonyl group, an alkenyloxycarbonyl group, an alkynyloxycarbonyl group, a benzyloxycarbonyl group or a 4-chlorobenzyloxycarbonyl group, $R^3$ is a hydrogen atom, a fluorine atom or a chlorine atom, $R^4$ is a chlorine atom, a bromine atom, a cyano group, a nitro group, a trifluoromethyl group, an alkylthio group, an alkylsulfinyl group, an alkylsulfonyl group, a haloalkoxy group or a haloalkylthio group, each of $R^5$ and $R^6$ is a hydrogen atom, Q is a methine group or a nitrogen atom, m is 1, n is 2, and r is 1.

More preferred are compounds of the formula (I) wherein $R^1$ is a chlorine atom and an ethyl group, $R^2$ is an alkynyl group, an alkoxycarbonyl group, an alkenyloxycarbonyl group, an alkynyloxycarbonyl group, a benzyloxycarbonyl group or a 4-chlorobenzyloxycarbonyl group, $R^3$ is a hydrogen atom, a fluorine atom or a chlorine atom, $R^4$ is a chlorine atom, a cyano group, a nitro group, a trifluoromethyl group, a methylthio group, a methylsulfinyl group, a methylsulfonyl group, a trifluoromethoxy group or a trifluoromethylthio group, each of $R^5$ and $R^6$ is a hydrogen atom, Q is a methine group or a nitrogen atom, m is 1, n is 2, and r is 1.

Still further preferred are compounds of the formula (I) wherein $R^1$ is a chlorine atom and an ethyl group, $R^2$ is a propargyl group, a methoxycarbonyl group or an allyloxycarbonyl group, $R^3$ is a hydrogen atom, $R^4$ is a chlorine atom, a cyano group, a nitro group or a trifluoromethyl group, each of $R^5$ and $R^6$ is a hydrogen atom, Q is a methine group or a nitrogen atom, m is, 1, n is 2, and r is 1.

Now, typical specific examples of the compounds of the formula (I) of the present invention will be given in Tables 1 to 17. However, it should be understood that the compounds of the present invention are not limited to such specific examples. The compound Nos. used in the Tables will be referred to in the subsequent description. In the Tables, the following alkyl groups will be abbreviated as follows:

| | | | |
|---|---|---|---|
| Methyl group: | Me | Ethyl group: | Et |
| Propyl group: | Pr | Isopropyl group: | Pr-i |
| Butyl group: | Bu | Isobutyl group: | Bu-i |
| sec-Butyl group: | Bu-sec | tert-Butyl group: | Bu-t |

TABLE 1

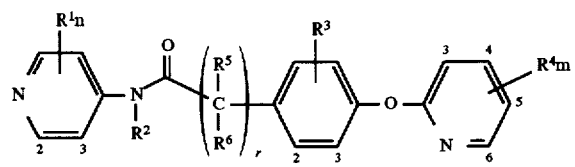

| Comp. No. | $R^1$n | $R^2$ | $R^3$ | $R^4$m | $R^5$ | $R^6$ | r | m.p. (°C.) or refractive index ($n_D^{20}$) |
|---|---|---|---|---|---|---|---|---|
| I-1 | H | COOMe | H | 5-CF$_3$ | H | H | 1 | |
| I-2 | H | COOMe | H | 5-CN | H | H | 1 | |
| I-3 | 2-Cl | COOMe | H | 5-CF$_3$ | H | H | 1 | |
| I-4 | 2-Cl | COOMe | H | 5-CN | H | H | 1 | |
| I-5 | 3-Cl | COOMe | H | 5-CF$_3$ | H | H | 1 | |
| I-6 | 3-Cl | COOMe | H | 5-CN | H | H | 1 | |
| I-7 | 2, 3-Cl$_2$ | COOMe | H | 5-CF$_3$ | H | H | 1 | |
| I-8 | 2, 3-Cl$_2$ | COOMe | H | 5-CN | H | H | 1 | |
| I-9 | 2, 5-Cl$_2$ | COOMe | H | 5-CF$_3$ | H | H | 1 | |
| I-10 | 2, 5-Cl$_2$ | COOMe | H | 5-CN | H | H | 1 | |
| I-11 | 2-Me | COOMe | H | 5-CF$_3$ | H | H | 1 | |
| I-12 | 2-Me | COOMe | H | 5-CN | H | H | 1 | |
| I-13 | 2, 3-(Me)$_2$ | COOMe | H | 5-CF$_3$ | H | H | 1 | |
| I-14 | 2, 3-(Me)$_2$ | COOMe | H | 5-CN | H | H | 1 | |
| I-15 | 2-Me, 3-Cl | COOMe | H | 5-CF$_3$ | H | H | 1 | 83–85 |
| I-16 | 2-Me, 3-Cl | COOMe | H | 5-CN | H | H | 1 | 38–40 |
| I-17 | 2-Et | COOMe | H | 5-CF$_3$ | H | H | 1 | |
| I-18 | 2-Et | COOMe | H | 5-CN | H | H | 1 | |
| I-19 | 3-C$_6$H$_{13}$ | COOMe | H | 5-CF$_3$ | H | H | 1 | |
| I-20 | 3-C$_6$H$_{13}$ | COOMe | H | 5-CN | H | H | 1 | |
| I-21 | 2-CF$_3$ | COOMe | H | 5-CF$_3$ | H | H | 1 | |
| I-22 | 2-CF$_3$ | COOMe | H | 5-CN | H | H | 1 | |
| I-23 | 2-◁ | COOMe | H | 5-CF$_3$ | H | H | 1 | |
| I-24 | 2-◁ | COOMe | H | 5-CN | H | H | 1 | |

TABLE 2

| Comp. No. | R¹n | R² | R³ | R⁴m | R⁵ | R⁶ | r | m.p. (°C.) or refractive index ($n_D^{20}$) |
|---|---|---|---|---|---|---|---|---|
| I-25 | 2-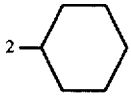 | COOMe | H | 5-$CF_3$ | H | H | 1 | |
| I-26 | 2-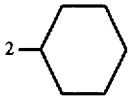 | COOMe | H | 5-CN | H | H | 1 | |
| I-27 | 2-OMe | COOMe | H | 5-$CF_3$ | H | H | 1 | |
| I-28 | 2-OMe | COOMe | H | 5-CN | H | H | 1 | |
| I-29 | 3-OMe | COOMe | H | 5-$CF_3$ | H | H | 1 | |
| I-30 | 3-OMe | COOMe | H | 5-CN | H | H | 1 | |
| I-31 | 2-OEt | COOMe | H | 5-$CF_3$ | H | H | 1 | |
| I-32 | 2-OEt | COOMe | H | 5-CN | H | H | 1 | |
| I-33 | 3-OEt | COOMe | H | 5-$CF_3$ | H | H | 1 | |
| I-34 | 3-OEt | COOMe | H | 5-CN | H | H | 1 | |
| I-35 | 3-Br, 2-Me | COOMe | H | 5-$CF_3$ | H | H | 1 | |
| I-36 | 3-Br, 2-Me | COOMe | H | 5-CN | H | H | 1 | |
| I-37 | 3-Br, 2-Et | COOMe | H | 5-$CF_3$ | H | H | 1 | |
| I-38 | 3-Br, 2-Et | COOMe | H | 5-CN | H | H | 1 | |
| I-39 | 3-Cl, 2-Et | COOEt | H | 5-$CF_3$ | H | H | 1 | 1.5269 |
| I-40 | 3-Cl, 2-Et | COOEt | H | 5-CN | H | H | 1 | |
| I-41 | 3-Cl, 2-Et | COOPr | H | 5-$CF_3$ | H | H | 1 | 1.5391 |
| I-42 | 3-Cl, 2-Et | COOPr | H | 5-CN | H | H | 1 | |
| I-43 | 3-Cl, 2-Et | COOPr-i | H | 5-$CF_3$ | H | H | 1 | 1.5165 |
| I-44 | 3-Cl, 2-Et | COOPr-i | H | 5-CN | H | H | 1 | |
| I-45 | 3-Cl, 2-Et | COOBu | H | 5-$CF_3$ | H | H | 1 | 1.5351 |
| I-46 | 3-Cl, 2-Et | COOBu | H | 5-CN | H | H | 1 | |
| I-47 | 3-Cl, 2-Et | COOBu-sec | H | 5-$CF_3$ | H | H | 1 | 1.5148 |
| I-48 | 3-Cl, 2-Et | COOBu-sec | H | 5-CN | H | H | 1 | |
| I-49 | 3-Cl, 2-Et | COOBu-i | H | 5-$CF_3$ | H | H | 1 | 1.5382 |
| I-50 | 3-Cl, 2-Et | COOBu-i | H | 5-CN | H | H | 1 | |
| I-51 | 3-Cl, 2-Et | $COOC_8H_{17}$ | H | 5-$CF_3$ | H | H | 1 | 1.5219 |
| I-52 | 3-Cl, 2-Et | $COOC_8H_{17}$ | H | 5-CN | H | H | 1 | |

TABLE 3

| Comp. No. | R¹n | R² | R³ | R⁴m | R⁵ | R⁶ | r | m.p. (°C.) or refractive index ($n_D^{20}$) |
|---|---|---|---|---|---|---|---|---|
| I-53 | 3-Cl, 2-Et | $COOCH_2CH=CH_2$ | H | 5-$CF_3$ | H | H | 1 | 1.5398 |
| I-54 | 3-Cl, 2-Et | $COOCH_2CH=CH_2$ | H | 5-CN | H | H | 1 | |
| I-55 | 3-Cl, 2-Et | $COOCH_2C\equiv CH$ | H | 5-$CF_3$ | H | H | 1 | 1.5418 |
| I-56 | 3-Cl, 2-Et | $COOCH_2C\equiv CH$ | H | 5-CN | H | H | 1 | |
| I-57 | 3-Cl, 2-Et | $COOCH_2CH_2OMe$ | H | 5-$CF_3$ | H | H | 1 | 1.5327 |
| I-58 | 3-Cl, 2-Et | $COOCH_2CH_2OMe$ | H | 5-CN | H | H | 1 | |
| I-59 | 3-Cl, 2-Et | $COOCH_2CH_2Cl$ | H | 5-$CF_3$ | H | H | 1 | 1.5399 |
| I-60 | 3-Cl, 2-Et | $COOCH_2CH_2Cl$ | H | 5-CN | H | H | 1 | |
| I-61 | 3-Cl, 2-Et | $COOCH_2$— | H | 5-$CF_3$ | H | H | 1 | |
| I-62 | 3-Cl, 2-Et | $COOCH_2$— | H | 5-CN | H | H | 1 | |
| I-63 | 3-Cl, 2-Et | COO—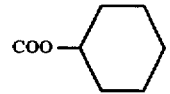 | H | 5-$CF_3$ | H | H | 1 | 1.5433 |
| I-64 | 3-Cl, 2-Et | COO—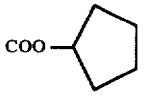 | H | 5-CN | H | H | 1 | |

TABLE 3-continued
| Comp. No. | R¹n | R² | R³ | R⁴m | R⁵ | R⁶ | r | m.p. (°C.) or refractive index ($n_D^{20}$) |
|---|---|---|---|---|---|---|---|---|
| I-65 | 3-Cl, 2-Et | 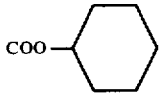 | H | 5-CF₃ | H | H | 1 | |
| I-66 | 3-Cl, 2-Et | 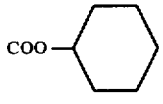 | H | 5-CN | H | H | 1 | |
| I-67 | 3-Cl, 2-Et | COOCH₂CF₃ | H | 5-CF₃ | H | H | 1 | |
| I-68 | 3-Cl, 2-Et | COOCH₂CF₃ | H | 5-CN | H | H | 1 | |
| I-69 | 3-Cl, 2-Et | 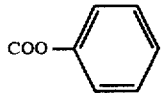 | H | 5-CF₃ | H | H | 1 | 34–35 |
| I-70 | 3-Cl, 2-Et | 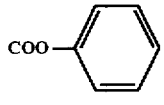 | H | 5-CN | H | H | 1 | |
| I-71 | 3-Cl, 2-Et | 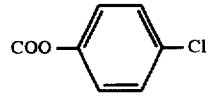 | H | 5-CF₃ | H | H | 1 | 1.5479 |
| I-72 | 3-Cl, 2-Et | 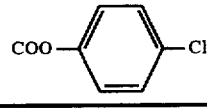 | H | 5-CN | H | H | 1 | |
TABLE 4
| Comp. No. | R¹n | R² | R³ | R⁴m | R⁵ | R⁶ | r | m.p. (°C.) or refractive index ($n_D^{20}$) |
|---|---|---|---|---|---|---|---|---|
| I-73 | 3-Cl, 2-Et | 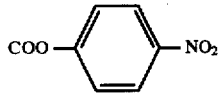 | H | 5-CF₃ | H | H | 1 | |
| I-74 | 3-Cl, 2-Et | 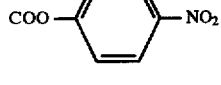 | H | 5-CN | H | H | 1 | |
| I-75 | 3-Cl, 2-Et | 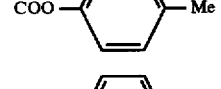 | H | 5-CF₃ | H | H | 1 | |
| I-76 | 3-Cl, 2-Et | 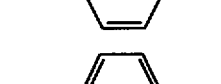 | H | 5-CN | H | H | 1 | |
| I-77 | 3-Cl, 2-Et |  | H | 5-CF₃ | H | H | 1 | |
| I-78 | 3-Cl, 2-Et |  | H | 5-CN | H | H | 1 | |

TABLE 4-continued

| Comp. No. | R¹n | R² | R³ | R⁴m | R⁵ | R⁶ | r | m.p. (°C.) or refractive index ($n_D^{20}$) |
|---|---|---|---|---|---|---|---|---|
| I-79 | 3-Cl, 2-Et | COO—C₆H₄—OMe | H | 5-CF₃ | H | H | 1 | |
| I-80 | 3-Cl, 2-Et | COO—C₆H₄—OMe | H | 5-CN | H | H | 1 | |
| I-81 | 3-Cl, 2-Et | COOCH₂—C₆H₅ | H | 5-CF₃ | H | H | 1 | 1.5368 |
| I-82 | 3-Cl, 2-Et | COOCH₂—C₆H₅ | H | 5-CN | H | H | 1 | |
| I-83 | 3-Cl, 2-Et | COOCH₂—C₆H₄—Cl | H | 5-CF₃ | H | H | 1 | 1.5499 |
| I-84 | 3-Cl, 2-Et | COOCH₂—C₆H₄—Cl | H | 5-CN | H | H | 1 | |
| I-85 | 3-Cl, 2-Et | COOCH₂—C₆H₄—NO₂ | H | 5-CF₃ | H | H | 1 | |
| I-86 | 3-Cl, 2-Et | COOCH₂—C₆H₄—NO₂ | H | 5-CN | H | H | 1 | |
| I-87 | 3-Cl, 2-Et | COOCH₂—C₆H₄—Me | H | 5-CF₃ | H | H | 1 | |

TABLE 5

| Comp. No. | R¹n | R² | R³ | R⁴m | R⁵ | R⁶ | r | m.p. (°C.) or refractive index ($n_D^{20}$) |
|---|---|---|---|---|---|---|---|---|
| I-88 | 3-Cl, 2-Et | COOCH₂—C₆H₄—Me | H | 5-CN | H | H | 1 | |
| I-89 | 3-Cl, 2-Et | COOCH₂—C₆H₄—CF₃ | H | 5-CF₃ | H | H | 1 | |
| I-90 | 3-Cl, 2-Et | COOCH₂—C₆H₄—CF₃ | H | 5-CN | H | H | 1 | |

TABLE 5-continued

| Comp. No. | $R^1n$ | $R^2$ | $R^3$ | $R^4m$ | $R^5$ | $R^6$ | r | m.p. (°C.) or refractive index ($n_D^{20}$) |
|---|---|---|---|---|---|---|---|---|
| I-91 | 3-Cl, 2-Et | COOCH$_2$—⌬—OMe | H | 5-CF$_3$ | H | H | 1 | |
| I-92 | 3-Cl, 2-Et | COOCH$_2$—⌬—OMe | H | 5-CN | H | H | 1 | |
| I-93 | 3-Cl, 2-Et | CH$_2$CH=CH$_2$ | H | 5-CF$_3$ | H | H | 1 | 1.5598 |
| I-94 | 3-Cl, 2-Et | CH$_2$CH=CH$_2$ | H | 5-CN | H | H | 1 | |
| I-95 | 3-Cl, 2-Et | CH$_2$C≡CH | H | 5-CF$_3$ | H | H | 1 | 1.5619 |
| I-96 | 3-Cl, 2-Et | CH$_2$C≡CH | H | 5-CN | H | H | 1 | 82–84 |
| I-97 | 3-Cl, 2-Et | CH$_2$OEt | H | 5-CF$_3$ | H | H | 1 | 1.5380 |
| I-98 | 3-Cl, 2-Et | CH$_2$OEt | H | 5-CN | H | H | 1 | |
| I-99 | 3-Cl, 2-Et | CH$_2$COOMe | H | 5-CF$_3$ | H | H | 1 | 1.5378 |
| I-100 | 3-Cl, 2-Et | CH$_2$COOMe | H | 5-CN | H | H | 1 | |
| I-101 | 3-Cl, 2-Et | COOMe | 3-Cl | 5-CF$_3$ | H | H | 1 | 1.5561 |
| I-102 | 3-Cl, 2-Et | COOMe | 3-Cl | 5-CN | H | H | 1 | |
| I-103 | 3-Cl, 2-Et | COOMe | 3-F | 5-CF$_3$ | H | H | 1 | 1.5434 |
| I-104 | 3-Cl, 2-Et | COOMe | 3-F | 5-CN | H | H | 1 | |
| I-105 | 3-Cl, 2-Et | COOMe | 2-Me | 5-CF$_3$ | H | H | 1 | |
| I-106 | 3-Cl, 2-Et | COOMe | 2-Me | 5-CN | H | H | 1 | |
| I-107 | 3-Cl, 2-Et | COOMe | 3-Me | 5-CF$_3$ | H | H | 1 | |
| I-108 | 3-Cl, 2-Et | COOMe | 3-Me | 5-CN | H | H | 1 | |
| I-109 | 3-Cl, 2-Me | COOMe | 3-OMe | 5-CF$_3$ | H | H | 1 | |
| I-110 | 3-Cl, 2-Me | COOMe | 3-OMe | 5-CN | H | H | 1 | |
| I-111 | 3-OCH$_2$CF$_3$ | COOMe | H | 5-CF$_3$ | H | H | 1 | |
| I-112 | 3-Cl, 2-Et | COOMe | H | H | H | H | 1 | |

TABLE 6

| Comp. No. | $R^1n$ | $R^2$ | $R^3$ | $R^4m$ | $R^5$ | $R^6$ | r | m.p. (°C.) or refractive index ($n_D^{20}$) |
|---|---|---|---|---|---|---|---|---|
| I-113 | 3-Cl, 2-Et | COOMe | H | 5-F | H | H | 1 | |
| I-114 | 3-Cl, 2-Et | COOMe | H | 5-Cl | H | H | 1 | 1.5776 |
| I-115 | 3-Cl, 2-Et | COOMe | H | 5-Br | H | H | 1 | 1.5849 |
| I-116 | 3-Cl, 2-Et | COOMe | H | 5-CN | H | H | 1 | 112–113 |
| I-117 | 3-Cl, 2-Et | COOMe | H | 5-NO$_2$ | H | H | 1 | 1.5979 |
| I-118 | 3-Cl, 2-Et | COOMe | H | 5-CF$_3$ | H | H | 1 | 62–64 |
| I-119 | 3-OCH$_2$CF$_3$ | COOMe | H | 5-CN | H | H | 1 | |
| I-120 | 3-Cl, 2-Et | COOMe | H | 5-COOMe | H | H | 1 | |
| I-121 | 3-Cl, 2-Et | COOMe | H | 5-COOEt | H | H | 1 | |
| I-122 | 3-Cl, 2-Et | COOMe | H | 5-COOCH$_2$CH$_2$Si(Me)$_3$ | H | H | 1 | |
| I-123 | 3-Cl, 2-Et | COOMe | H | 5-COOPr | H | H | 1 | |
| I-124 | 3-Cl, 2-Et | COOMe | H | 5-COOPr-i | H | H | 1 | |
| I-125 | 3-Cl, 2-Et | COOMe | H | 5-COOBu | H | H | 1 | |
| I-126 | 3-Cl, 2-Et | COOMe | H | 3-COOCH$_2$—⌬ | H | H | 1 | |
| I-127 | 3-Cl, 2-Et | COOMe | H | 5-COOCH$_2$—⌬ | H | H | 1 | |
| I-128 | 3-Cl, 2-Et | COOMe | H | 3, 5-Cl$_2$ | H | H | 1 | |
| I-129 | 3-Cl, 2-Et | COOMe | H | 3-Cl, 5-CF$_3$ | H | H | 1 | 1.5601 |
| I-130 | 3-Cl, 2-Et | COOMe | H | 5-CF$_3$ | Me | H | 1 | |
| I-131 | 3-Cl, 2-Et | COOMe | H | 5-CN | Me | H | 1 | |
| I-132 | 3-Cl, 2-Et | COOMe | 3-Cl | 5-CF$_3$ | Me | H | 1 | |
| I-133 | 3-Cl, 2-Et | COOMe | 3-Cl | 5-CN | Me | H | 1 | |
| I-134 | 3-Cl, 2-Et | COOMe | 3-F | 5-CF$_3$ | Me | H | 1 | |
| I-135 | 3-Cl, 2-Et | COOMe | 3-F | 5-CN | Me | H | 1 | |
| I-136 | 3-Cl, 2-Et | COOMe | H | 5-CF$_3$ | Me | Me | 1 | |

TABLE 6-continued

| Comp. No. | R¹n | R² | R³ | R⁴m | R⁵ | R⁶ | r | m.p. (°C.) or refractive index ($n_D^{20}$) |
|---|---|---|---|---|---|---|---|---|
| I-137 | 3-Cl, 2-Et | COOMe | H | 5-CN | Me | Me | 1 | |
| I-138 | 3-Cl, 2-Et | COOMe | 3-Cl | 5-CF₃ | Me | Me | 1 | |
| I-139 | 3-Cl, 2-Et | COOMe | 3-Cl | 5-CN | Me | Me | 1 | |
| I-140 | 3-Cl, 2-Et | COOMe | H | 5-CF₃ | Pr-i | H | 1 | 1.5372 |

TABLE 7

| Comp. No. | R¹n | R² | R³ | R⁴m | R⁵ | R⁶ | r | m.p. (°C.) or refractive index ($n_D^{20}$) |
|---|---|---|---|---|---|---|---|---|
| I-141 | 3-Cl, 2-Et | COOMe | H | 5-CN | Pr-i | H | 1 | |
| I-142 | 3-Cl, 2-Et | COOMe | 3-Cl | 5-CF₃ | Pr-i | H | 1 | |
| I-143 | 3-Cl, 2-Et | COOMe | 3-Cl | 5-CN | Pr-i | H | 1 | |
| I-144 | 3-Cl, 2-Et | COOMe | 3-F | 5-CF₃ | Pr-i | H | 1 | |
| I-145 | 3-Cl, 2-Et | COOMe | 3-F | 5-CN | Pr-i | H | 1 | |
| I-146 | 3-Cl, 2-Et | COOMe | H | 5-CF₃ | H | H | 2 | |
| I-147 | 3-Cl, 2-Et | COOMe | H | 5-CF₃ | H | H | 3 | |
| I-148 | 3-Cl, 2-Et | COOMe | H | 5-CF₃ | H | H | 4 | |
| I-149 | 3-Cl, 2-Et | COOBu-t | H | 5-Cl | H | H | 1 | |
| I-150 | 3-Cl, 2-Et | COOBu-t | H | 5-CF₃ | H | H | 1 | |
| I-151 | 3-Cl, 2-Et | COOBu-t | H | 5-CN | H | H | 1 | |

TABLE 8

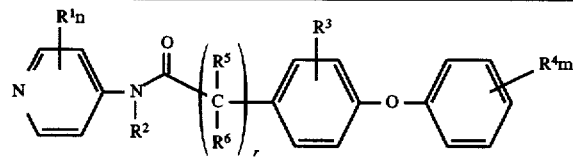

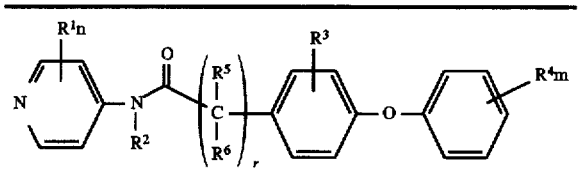

| Comp. No. | R¹n | R² | R³ | R⁴m | R⁵ | R⁶ | r | m.p.(°C.) or refractive index ($n_D^{20}$) |
|---|---|---|---|---|---|---|---|---|
| II-1 | H | COOMe | H | 4-CF₃ | H | H | 1 | |
| II-2 | H | COOMe | H | 4-CF₃ | H | H | 1 | |
| II-3 | 2-Cl | COOMe | H | 4-CF₃ | H | H | 1 | |
| II-4 | 2-Cl | COOMe | H | 4-Cl | H | H | 1 | |
| II-5 | 3-Cl | COOMe | H | 4-CF₃ | H | H | 1 | |
| II-6 | 3-Cl | COOMe | H | 4-Cl | H | H | 1 | |
| II-7 | 2,3-Cl₂ | COOMe | H | 4-CF₃ | H | H | 1 | |
| II-8 | 2,3-Cl₂ | COOMe | H | 4-Cl | H | H | 1 | |
| II-9 | 2,5-Cl₂ | COOMe | H | 4-CF₃ | H | H | 1 | |
| II-10 | 2,5-Cl₂ | COOMe | H | 4-Cl | H | H | 1 | |
| II-11 | 2-Me | COOMe | H | 4-CF₃ | H | H | 1 | |
| II-12 | 2-Me | COOMe | H | 4-Cl | H | H | 1 | |
| II-13 | 2,3-(Me)₂ | COOMe | H | 4-CF₃ | H | H | 1 | |
| II-14 | 2,3-(Me)₂ | COOMe | H | 4-Cl | H | H | 1 | |
| II-15 | 2-Me, 3-Cl | COOMe | H | 4-CF₃ | H | H | 1 | |
| II-16 | 2-Me, 3-Cl | COOMe | H | 4-Cl | H | H | 1 | |
| II-17 | 2-Et | COOMe | H | 4-CF₃ | H | H | 1 | |
| II-18 | 2-Et | COOMe | H | 4-Cl | H | H | 1 | |
| II-19 | 3-C₆H₁₃ | COOMe | H | 4-CF₃ | H | H | 1 | |
| II-20 | 3-C₆H₁₃ | COOMe | H | 4-Cl | H | H | 1 | |
| II-21 | 2-CF₃ | COOMe | H | 4-CF₃ | H | H | 1 | |
| II-22 | 2-CF₃ | COOMe | H | 4-Cl | H | H | 1 | |
| II-23 | 2-(cyclopropyl) | COOMe | H | 4-CF₃ | H | H | 1 | |
| II-24 | 2-(cyclopropyl) | COOMe | H | 4-Cl | H | H | 1 | |

TABLE 9

| Comp. No. | R¹n | R² | R³ | R⁴m | R⁵ | R⁶ | r | m.p.(°C.) or refractive index ($n_D^{20}$) |
|---|---|---|---|---|---|---|---|---|
| II-25 | 2-(cyclohexyl) | COOMe | H | 4-CF₃ | H | H | 1 | |

TABLE 9-continued

| Comp. No. | R¹n | R² | R³ | R⁴m | R⁵ | R⁶ | r | m.p.(°C.) or refractive index ($n_D^{20}$) |
|---|---|---|---|---|---|---|---|---|
| II-25 | 2-(cyclohexyl) | COOMe | H | 4-CF₃ | H | H | 1 | |
| II-27 | 2-OMe | COOMe | H | 4-CF₃ | H | H | 1 | |
| II-28 | 2-OMe | COOMe | H | 4-Cl | H | H | 1 | |
| II-29 | 3-OMe | COOMe | H | 4-CF₃ | H | H | 1 | |
| II-30 | 3-OMe | COOMe | H | 4-Cl | H | H | 1 | |
| II-31 | 2-OEt | COOMe | H | 4-CF₃ | H | H | 1 | |
| II-32 | 2-OEt | COOMe | H | 4-Cl | H | H | 1 | |
| II-33 | 3-OEt | COOMe | H | 4-CF₃ | H | H | 1 | |
| II-34 | 3-OEt | COOMe | H | 4-Cl | H | H | 1 | |
| II-35 | 3-Br, 2-Me | COOMe | H | 4-CF₃ | H | H | 1 | |
| II-36 | 3-Br, 2-Me | COOMe | H | 4-Cl | H | H | 1 | |
| II-37 | 3-Br, 2-Et | COOMe | H | 4-CF₃ | H | H | 1 | |
| II-38 | 3-Br, 2-Et | COOMe | H | 4-Cl | H | H | 1 | |
| II-39 | 3-Cl, 2-Et | COOEt | H | 4-CF₃ | H | H | 1 | Unmeasurable |
| II-40 | 3-Cl, 2-Et | COOEt | H | 4-Cl | H | H | 1 | 1.5811 |
| II-41 | 3-Cl, 2-Et | COOPr | H | 4-CF₃ | H | H | 1 | 1.5392 |
| II-42 | 3-Cl, 2-Et | COOPr | H | 4-Cl | H | H | 1 | 1.5752 |
| II-43 | 3-Cl, 2-Et | COOPr-i | H | 4-CF₃ | H | H | 1 | 1.5325 |
| II-44 | 3-Cl, 2-Et | COOPr-i | H | 4-Cl | H | H | 1 | 1.5718 |
| II-45 | 3-Cl, 2-Et | COOBu | H | 4-CF₃ | H | H | 1 | |
| II-46 | 3-Cl, 2-Et | COOBu | H | 4-Cl | H | H | 1 | 1.5691 |
| II-47 | 3-Cl, 2-Et | COOBu-sec | H | 4-CF₃ | H | H | 1 | |
| II-48 | 3-Cl, 2-Et | COOBu-sec | H | 4-Cl | H | H | 1 | 1.5671 |
| II-49 | 3-Cl, 2-Et | COOBu-i | H | 4-CF₃ | H | H | 1 | |
| II-50 | 3-Cl, 2-Et | COOBu-i | H | 4-Cl | H | H | 1 | 1.5559 |
| II-51 | 3-Cl, 2-Et | COOC₈H₁₇ | H | 4-CF₃ | H | H | 1 | |
| II-52 | 3-Cl, 2-Et | COOC₈H₁₇ | H | 4-Cl | H | H | 1 | 1.5511 |

TABLE 10

| Comp. No. | R¹n | R² | R³ | R⁴m | R⁵ | R⁶ | r | m.p.(°C.) or refractive index ($n_D^{20}$) |
|---|---|---|---|---|---|---|---|---|
| II-53 | 3-Cl, 2-Et | COOCH₂CH=CH₂ | H | 4-CF₃ | H | H | 1 | 1.5479 |
| II-54 | 3-Cl, 2-Et | COOCH₂CH=CH₂ | H | 4-Cl | H | H | 1 | 1.5479 |
| II-55 | 3-Cl, 2-Et | COOCH₂C≡CH₂ | H | 4-CF₃ | H | H | 1 | 1.5793 |
| II-56 | 3-Cl, 2-Et | COOCH₂C≡CH₂ | H | 4-Cl | H | H | 1 | 1.5531 |
| II-57 | 3-Cl, 2-Et | COOCH₂CH₂OMe | H | 4-CF₃ | H | H | 1 | 1.5836 |
| II-58 | 3-Cl, 2-Et | COOCH₂CH₂OMe | H | 4-Cl | H | H | 1 | 1.5441 |
| II-59 | 3-Cl, 2-Et | COOCH₂CH₂Cl | H | 4-CF₃ | H | H | 1 | 1.5748 |
| II-60 | 3-Cl, 2-Et | COOCH₂CH₂Cl | H | 4-Cl | H | H | 1 | 1.5529 |
| II-61 | 3-Cl, 2-Et | COOCH₂-(cyclopropyl) | H | 4-CF₃ | H | H | 1 | 1.5872 |
| II-62 | 3-Cl, 2-Et | COOCH₂-(cyclopropyl) | H | 4-Cl | H | H | 1 | |
| II-63 | 3-Cl, 2-Et | COO-(cyclopentyl) | H | 4-CF₃ | H | H | 1 | |
| II-64 | 3-Cl, 2-Et | COO-(cyclopentyl) | H | 4-Cl | H | H | 1 | 1.5778 |
| II-65 | 3-Cl, 2-Et | COO-(cyclohexyl) | H | 4-CF₃ | H | H | 1 | |

TABLE 10-continued

| Comp. No. | $R^1n$ | $R^2$ | $R^3$ | $R^4m$ | $R^5$ | $R^6$ | r | m.p.(°C.) or refractive index ($n_D^{20}$) |
|---|---|---|---|---|---|---|---|---|
| II-66 | 3-Cl, 2-Et | 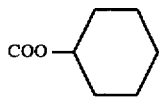COO— | H | 4-Cl | H | H | 1 | |
| II-67 | 3-Cl, 2-Et | COOCH$_2$CF$_3$ | H | 4-CF$_3$ | H | H | 1 | |
| II-68 | 3-Cl, 2-Et | COOCH$_2$CF$_3$ | H | 4-Cl | H | H | 1 | 1.5498 |
| II-69 | 3-Cl, 2-Et | 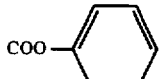COO— | H | 4-CF$_3$ | H | H | 1 | |
| II-70 | 3-Cl, 2-Et | 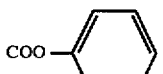COO— | H | 4-Cl | H | H | 1 | 1.6039 |
| II-71 | 3-Cl, 2-Et | 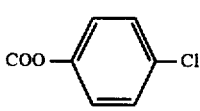COO—Cl | H | 4-CF$_3$ | H | H | 1 | |
| II-72 | 3-Cl, 2-Et | 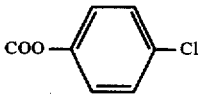COO—Cl | H | 4-Cl | H | H | 1 | 1.5982 |

TABLE 11

| Comp. No. | $R^1n$ | $R^2$ | $R^3$ | $R^4m$ | $R^5$ | $R^6$ | r | m.p.(°C.) or refractive index ($n_D^{20}$) |
|---|---|---|---|---|---|---|---|---|
| II-73 | 3-Cl, 2-Et | 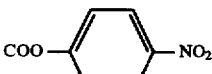COO—NO$_2$ | H | 4-CF$_3$ | H | H | 1 | |
| II-74 | 3-Cl, 2-Et | 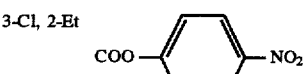COO—NO$_2$ | H | 4-Cl | H | H | 1 | |
| II-75 | 3-Cl, 2-Et | 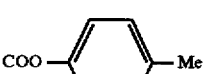COO—Me | H | 4-CF$_3$ | H | H | 1 | |
| II-76 | 3-Cl, 2-Et | 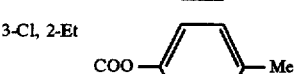COO—Me | H | 4-Cl | H | H | 1 | |
| II-77 | 3-Cl, 2-Et | COO—CF$_3$ | H | 4-CF$_3$ | H | H | 1 | |
| II-78 | 3-Cl, 2-Et | COO—CF$_3$ | H | 4-Cl | H | H | 1 | |
| II-79 | 3-Cl, 2-Et | 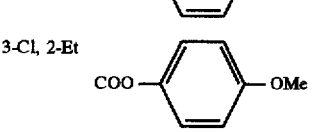COO—OMe | H | 4-CF$_3$ | H | H | 1 | |

TABLE 11-continued

| Comp. No. | R¹n | R² | R³ | R⁴m | R⁵ | R⁶ | r | m.p.(°C.) or refractive index ($n_D^{20}$) |
|---|---|---|---|---|---|---|---|---|
| II-80 | 3-Cl, 2-Et | COO—⟨C₆H₄⟩—OMe | H | 4-Cl | H | H | 1 | |
| II-81 | 3-Cl, 2-Et | COOCH₂—⟨C₆H₅⟩ | H | 4-CF₃ | H | H | 1 | 1.5679 |
| II-82 | 3-Cl, 2-Et | COOCH₂—⟨C₆H₅⟩ | H | 4-Cl | H | H | 1 | 1.5992 |
| II-83 | 3-Cl, 2-Et | COOCH₂—⟨C₆H₄⟩—Cl | H | 4-CF₃ | H | H | 1 | 1.5692 |
| II-84 | 3-Cl, 2-Et | COOCH₂—⟨C₆H₄⟩—Cl | H | 4-Cl | H | H | 1 | 1.6010 |
| II-85 | 3-Cl, 2-Et | COOCH₂—⟨C₆H₄⟩—NO₂ | H | 4-CF₃ | H | H | 1 | |
| II-86 | 3-Cl, 2-Et | COOCH₂—⟨C₆H₄⟩—NO₂ | H | 4-Cl | H | H | 1 | |
| II-87 | 3-Cl, 2-Et | COOCH₂—⟨C₆H₄⟩—Me | H | 4-CF₃ | H | H | 1 | |

TABLE 12

| Comp. No. | R¹n | R² | R³ | R⁴m | R⁵ | R⁶ | r | m.p.(°C.) or refractive index ($n_D^{20}$) |
|---|---|---|---|---|---|---|---|---|
| II-88 | 3-Cl, 2-Et | COOCH₂—⟨C₆H₄⟩—Me | H | 4-Cl | H | H | 1 | |
| II-89 | 3-Cl, 2-Et | COOCH₂—⟨C₆H₄⟩—CF₃ | H | 4-CF₃ | H | H | 1 | |
| II-90 | 3-Cl, 2-Et | COOCH₂—⟨C₆H₄⟩—CF₃ | H | 4-Cl | H | H | 1 | |
| II-91 | 3-Cl, 2-Et | COOCH₂—⟨C₆H₄⟩—OMe | H | 4-CF₃ | H | H | 1 | |

TABLE 12-continued

| Comp. No. | R¹n | R² | R³ | R⁴m | R⁵ | R⁶ | r | m.p.(°C.) or refractive index ($n_D^{20}$) |
|---|---|---|---|---|---|---|---|---|
| II-92 | 3-Cl, 2-Et | COOCH₂—⟨C₆H₄⟩—OMe | H | 4-Cl | H | H | 1 | |
| II-93 | 3-Cl, 2-Et | CH₂CH=CH₂ | H | 4-CF₃ | H | H | 1 | |
| II-94 | 3-Cl, 2-Et | CH₂CH=CH₂ | H | 4-Cl | H | H | 1 | |
| II-95 | 3-Cl, 2-Et | CH₂C≡CH | H | 4-CF₃ | H | H | 1 | 1.5912 |
| II-96 | 3-Cl, 2-Et | CH₂C≡CH | H | 4-Cl | H | H | 1 | 91–92 |
| II-97 | 3-Cl, 2-Et | CH₂OEt | H | 4-CF₃ | H | H | 1 | |
| II-98 | 3-Cl, 2-Et | CH₂OEt | H | 4-Cl | H | H | 1 | |
| II-99 | 3-Cl, 2-Et | CH₂COOMe | H | 4-CF₃ | H | H | 1 | |
| II-100 | 3-Cl, 2-Et | CH₂COOMe | H | 4-Cl | H | H | 1 | |
| II-101 | 3-Cl, 2-Et | COOMe | 3-Cl | 4-CF₃ | H | H | 1 | |
| II-102 | 3-Cl, 2-Et | COOMe | 3-Cl | 4-Cl | H | H | 1 | |
| II-103 | 3-Cl, 2-Et | COOMe | 3-F | 4-CF₃ | H | H | 1 | |
| II-104 | 3-Cl, 2-Et | COOMe | 3-F | 4-Cl | H | H | 1 | |
| II-105 | 3-Cl, 2-Et | COOMe | 2-Me | 4-CF₃ | H | H | 1 | |
| II-106 | 3-Cl, 2-Et | COOMe | 2-Me | 4-Cl | H | H | 1 | |
| II-107 | 3-Cl, 2-Et | COOMe | 3-Me | 4-CF₃ | H | H | 1 | |
| II-108 | 3-Cl, 2-Et | COOMe | 3-Me | 4-Cl | H | H | 1 | |
| II-109 | 3-Cl, 2-Et | COOMe | 3-OMe | 4-CF₃ | H | H | 1 | |
| II-110 | 3-Cl, 2-Et | COOMe | 3-OMe | 4-Cl | H | H | 1 | |
| II-111 | 3-OCH₂CF₃ | COOMe | H | 4-Cl | H | H | 1 | |
| II-112 | 3-Cl, 2-Et | COOMe | H | H | H | H | 1 | |

TABLE 13

| Comp. No. | R¹n | R² | R³ | R⁴m | R⁵ | R⁶ | r | m.p.(°C.) or refractive index ($n_D^{20}$) |
|---|---|---|---|---|---|---|---|---|
| II-113 | 3-Cl, 2-Et | COOMe | H | 4-F | H | H | 1 | |
| II-114 | 3-Cl, 2-Et | COOMe | H | 4-Cl | H | H | 1 | 1.5813 |
| II-115 | 3-Cl, 2-Et | COOMe | H | 4-Br | H | H | 1 | |
| II-116 | 3-Cl, 2-Et | COOMe | H | 4-CN | H | H | 1 | 73–76 |
| II-117 | 3-Cl, 2-Et | COOMe | H | 4-NO₂ | H | H | 1 | 126–127 |
| II-118 | 3-Cl, 2-Et | COOMe | H | 4-CF₃ | H | H | 1 | 1.5525 |
| II-119 | 3-OCH₂CF₃ | COOMe | H | 4-CN | H | H | 1 | |
| II-120 | 3-Cl, 2-Et | COOMe | H | 4-COOMe | H | H | 1 | |
| II-121 | 3-Cl, 2-Et | COOMe | H | 4-COOEt | H | H | 1 | |
| II-122 | 3-Cl, 2-Et | COOMe | H | 4-COOCH₂CH₂Si(Me)₃ | H | H | 1 | |
| II-123 | 3-Cl, 2-Et | COOMe | H | 4-COOPr | H | H | 1 | |
| II-124 | 3-Cl, 2-Et | COOMe | H | 4-COOPr-i | H | H | 1 | |
| II-125 | 3-Cl, 2-Et | COOMe | H | 4-COOBu | H | H | 1 | |
| II-126 | 3-Cl, 2-Et | COOMe | H | 4-CH₃ | H | H | 1 | 1.5723 |
| II-127 | 3-Cl, 2-Et | COOMe | H | 4-COOCH₂—⟨C₆H₅⟩ | H | H | 1 | |
| II-128 | 3-Cl, 2-Et | COOMe | H | 2,3-Cl₂ | H | H | 1 | |
| II-129 | 3-Cl, 2-Et | COOMe | H | 2-Cl, 4-CF₃ | H | H | 1 | |
| II-130 | 3-Cl, 2-Et | COOMe | H | 4-CF₃ | Me | H | 1 | |
| II-131 | 3-Cl, 2-Et | COOMe | H | 4-Cl | Me | H | 1 | |
| II-132 | 3-Cl, 2-Et | COOMe | 3-Cl | 4-CF₃ | Me | H | 1 | |
| II-133 | 3-Cl, 2-Et | COOMe | 3-Cl | 4-Cl | Me | H | 1 | |
| II-134 | 3-Cl, 2-Et | COOMe | 3-F | 4-CF₃ | Me | H | 1 | |
| II-135 | 3-Cl, 2-Et | COOMe | 3-F | 4-Cl | Me | H | 1 | |
| II-136 | 3-Cl, 2-Et | COOMe | H | 4-CF₃ | Me | Me | 1 | |
| II-137 | 3-Cl, 2-Et | COOMe | H | 4-Cl | Me | Me | 1 | |
| II-138 | 3-Cl, 2-Et | COOMe | 3-Cl | 4-CF₃ | Me | Me | 1 | |
| II-139 | 3-Cl, 2-Et | COOMe | 3-Cl | 4-Cl | Me | Me | 1 | |
| II-140 | 3-Cl, 2-Et | COOMe | H | 4-CF₃ | Pr-i | H | 1 | |

TABLE 14

| Comp. No. | $R^1n$ | $R^2$ | $R^3$ | $R^4n$ | $R^5$ | $R^6$ | r | m.p.(°C.) or refractive index ($n_D^{20}$) |
|---|---|---|---|---|---|---|---|---|
| II-141 | 3-Cl, 2-Et | COOMe | H | 4-Cl | Pr-i | H | 1 | |
| II-142 | 3-Cl, 2-Et | COOMe | 3-Cl | 4-CF$_3$ | Pr-i | H | 1 | |
| II-143 | 3-Cl, 2-Et | COOMe | 3-Cl | 4-Cl | Pr-i | H | 1 | |
| II-144 | 3-Cl, 2-Et | COOMe | 3-F | 4-CF$_3$ | Pr-i | H | 1 | |
| II-145 | 3-Cl, 2-Et | COOMe | 3-F | 4-Cl | Pr-i | H | 1 | |
| II-146 | 3-Cl, 2-Et | COOMe | H | 4-CF$_3$ | H | H | 2 | |
| II-147 | 3-Cl, 2-Et | COOMe | H | 4-CF$_3$ | H | H | 3 | |
| II-148 | 3-Cl, 2-Et | COOMe | H | 4-CF$_3$ | H | H | 4 | |
| II-149 | 3-Cl, 2-Et | COOBu-t | H | 4-Cl | H | H | 1 | |
| II-150 | 3-Cl, 2-Et | COOBu-t | H | 4-CF$_3$ | H | H | 1 | |
| II-151 | 3-Cl, 2-Et | COOBu-t | H | 4-CN | H | H | 1 | |
| II-152 | 3-Cl, 2-Et | COOPr-i | H | 4-CN | H | H | 1 | 1.5729 |
| II-153 | 3-Cl, 2-Et | COOCH$_2$CH=CH$_2$ | H | 4-CN | H | H | 1 | 1.5874 |
| II-154 | 3-Cl, 2-Et | CH$_2$C≡CH | H | 4-CN | H | H | 1 | 1.6045 |
| II-155 | 3-Cl, 2-Et | COOCH$_2$—C$_6$H$_4$—Cl | H | 4-CN | H | H | 1 | 1.5875 |
| II-156 | 3-Cl, 2-Et | CH$_2$C≡CH | H | 4-NO$_2$ | H | H | 1 | 103–105 |
| II-157 | 3-Cl, 2-Et | COOCH$_2$CH=CH$_2$ | H | 4-CN | Me | H | 1 | 1.5800 |
| II-158 | 3-Cl, 2-Et | COOMe | H | 4-CN | Me | H | 1 | 1.5859 |
| II-159 | 3-Cl, 2-Et | CH$_2$C≡CH | H | 4-OMe | H | H | 1 | 1.5925 |
| II-160 | 3-Cl, 2-Et | CH$_2$CH$_2$OMe | H | 4-Cl | H | H | 1 | 1.5869 |
| II-161 | 3-Cl, 2-Et | COOMe | H | 4-SMe | H | H | 1 | 1.6033 |
| II-162 | 3-Cl, 2-Et | CH$_2$C≡CH | H | 4-SMe | H | H | 1 | 1.6132 |
| II-163 | 3-Cl, 2-Et | COOCH$_2$CH=CH$_2$ | H | 4-SMe | H | H | 1 | 1.5911 |
| II-164 | 3-Cl, 2-Et | COOEt | H | 4-CN | H | H | 1 | 1.5844 |
| II-165 | 3-Cl, 2-Et | COOPr | H | 4-CN | H | H | 1 | 1.5775 |
| II-166 | 3-Cl, 2-Et | COOCH$_2$CH$_2$OMe | H | 4-CN | H | H | 1 | 1.5578 |
| II-167 | 3-Cl, 2-Et | COOCH$_2$C≡CH | H | 4-CN | H | H | 1 | 1.5628 |
| II-168 | 3-Cl, 2-Et | COOCH$_2$CH$_2$Cl | H | 4-CN | H | H | 1 | 1.5739 |
| II-169 | 3-Cl, 2-Et | COOCH$_2$—C$_6$H$_5$ | H | 4-CN | H | H | 1 | 1.5990 |

TABLE 15

| Comp. No. | $R^1n$ | $R^2$ | $R^3$ | $R^4m$ | $R^5$ | $R^6$ | r | m.p.(°C.) or refractive index ($n_D^{20}$) |
|---|---|---|---|---|---|---|---|---|
| II-170 | 3-Cl, 2-Et | COOMe | 3-Cl | 4-CN | H | H | 1 | 43–45 |
| II-171 | 3-Cl, 2-Et | COOCH$_2$CH=CH$_2$ | 3-Cl | 4-CN | H | H | 1 | 1.5861 |
| II-172 | 3-Cl, 2-Et | CH$_2$C≡CH | 3-Cl | 4-CN | H | H | 1 | 1.5999 |
| II-173 | 3-Cl, 2-Et | COOMe | 3-F | 4-CN | H | H | 1 | 1.5810 |
| II-174 | 3-Cl, 2-Et | COOCH$_2$CH=CH$_2$ | 3-F | 4-CN | H | H | 1 | 1.5770 |
| II-175 | 3-Cl, 2-Et | CH$_2$C≡CH | 3-F | 4-CN | H | H | 1 | 78–79 |
| II-176 | 3-Cl, 2-Et | COOMe | 3-OMe | 4-CN | H | H | 1 | 1.5828 |
| II-177 | 3-Cl, 2-Et | COOCH$_2$CH=CH$_2$ | 3-OMe | 4-CN | H | H | 1 | 1.5849 |
| II-178 | 3-Cl, 2-Et | CH$_2$C≡CH | 3-OMe | 4-CN | H | H | 1 | 1.5930 |
| II-179 | 3-Cl, 2-Et | COOMe | H | 2-Cl, 4-CN | H | H | 1 | 1.6001 |
| II-180 | 3-Cl, 2-Et | COOMe | H | 3-Cl, 4-CN | H | H | 1 | 1.5931 |
| II-181 | 3-Cl, 2-Et | COOCH$_2$CH=CH$_2$ | H | 2-Cl, 4-CN | H | H | 1 | 1.5928 |
| II-182 | 3-Cl, 2-Et | COOCH$_2$CH=CH$_2$ | H | 3-Cl, 4-CN | H | H | 1 | 1.5909 |
| II-183 | 3-Cl, 2-Et | CH$_2$C≡CH | H | 2-Cl, 4-CN | H | H | 1 | 1.6041 |
| II-184 | 3-Cl, 2-Et | CH$_2$C≡CH | H | 3-Cl, 4-CN | H | H | 1 | 64–65 |
| II-185 | 3-Cl, 2-Et | COOMe | H | 4-SOMe | H | H | 1 | 1.5870 |
| II-186 | 3-Cl, 2-Et | COOCH$_2$CH=CH$_2$ | H | 4-SOMe | H | H | 1 | 1.5942 |

TABLE 15-continued

| Comp. No. | R¹n | R² | R³ | R⁴m | R⁵ | R⁶ | r | m.p.(°C.) or refractive index ($n_D^{20}$) |
|---|---|---|---|---|---|---|---|---|
| II-187 | 3-Cl, 2-Et | CH₂C≡CH | H | 4-SOMe | H | H | 1 | 1.5458 |
| II-188 | 3-Cl, 2-Et | COOMe | H | 4-SO₂Me | H | H | 1 | 52–54 |
| II-189 | 3-Cl, 2-Et | COOCH₂CH=CH₂ | H | 4-SO₂Me | H | H | 1 | 1.5721 |
| II-190 | 3-Cl, 2-Et | CH₂C≡CH | H | 4-SO₂Me | H | H | 1 | 1.5881 |
| II-191 | 3-Cl, 2-Et | COOMe | H | 4-OCF₃ | H | H | 1 | 1.5492 |
| II-192 | 3-Cl, 2-Et | COOMe | H | 4-SCF₃ | H | H | 1 | 1.5681 |
| II-193 | 3-Cl, 2-Et | SN(Bu)₂ | H | 4-Cl | H | H | 1 | |
| II-194 | 3-Cl, 2-Et | SN(Bu)₂ | H | 4-CF₃ | H | H | 1 | |
| II-195 | 3-Cl, 2-Et | SN(Bu)₂ | H | 4-NO₂ | H | H | 1 | |
| II-196 | 3-Cl, 2-Et | SN(Bu)₂ | H | 4-CN | H | H | 1 | |
| II-197 | 3-Cl, 2-Et | SN(Pr-i)CH₂CH₂COOEt | H | 4-Cl | H | H | 1 | |
| II-198 | 3-Cl, 2-Et | SN(Pr-i)CH₂CH₂COOEt | H | 4-CF₃ | H | H | 1 | |
| II-199 | 3-Cl, 2-Et | SN(Pr-i)CH₂CH₂COOEt | H | 4-NO₂ | H | H | 1 | |

TABLE 16

| Comp. No. | R¹n | R² | R³ | R⁴m | R⁵ | R⁶ | r | m.p. (°C.) or refractive index ($n_D^{20}$) |
|---|---|---|---|---|---|---|---|---|
| II-200 | 3-Cl, 2-Et | SN(Pr-i)CH₂CH₂COOEt | H | 4-CN | H | H | 1 | |
| II-201 | 3-Cl, 2-Et | SN(Me)COOBu | H | 4-Cl | H | H | 1 | |
| II-202 | 3-Cl, 2-Et | SN(Me)COOBu | H | 4-CF₃ | H | H | 1 | |
| II-203 | 3-Cl, 2-Et | SN(Me)COOBu | H | 4-NO₂ | H | H | 1 | |
| II-204 | 3-Cl, 2-Et | SN(Me)COOBu | H | 4-CN | H | H | 1 | |

TABLE 17

| Comp. No. | Structure | m.p.(°C.) or refractive index ($n_D^{20}$) |
|---|---|---|
| III-1 | Et, Cl substituted pyridyl–N(COOCH₃)–C(=O)–CH₂–C₆H₄–O–(3-pyridyl with 2-CN) | |
| III-2 | Et, Cl substituted pyridyl–N(COOCH₃)–C(=O)–CH₂–C₆H₄–O–(4-pyridyl with 2-CN) | |
| III-3 | Et, Cl substituted pyridyl–N(COOCH₃)–C(=O)–CH₂–C₆H₄–O–(3-pyridyl with 2-CN) | |
| III-4 | Et, Cl substituted pyridyl–N(COOCH₃)–C(=O)–CH₂–C₆H₄–O–(4-pyridyl with 2-CN) | |

TABLE 17-continued

| Comp. No. | Structure | m.p.(°C.) or refractive index ($n_D^{20}$) |
|---|---|---|
| III-5 | ![III-5 structure: Et, Cl on pyridine N-C(=O)CH2-phenyl-O-pyridine-CF3, with N-COOCH3] | |
| III-6 | ![III-6 structure: Et, Cl on pyridine N-C(=O)CH2-phenyl-O-pyridine-Cl, with N-COOCH3] | |

The compounds of the formula (I) of the present invention can be produced in accordance with the following processes. However, the method for their production is not limited to such specific processes.

Process 1

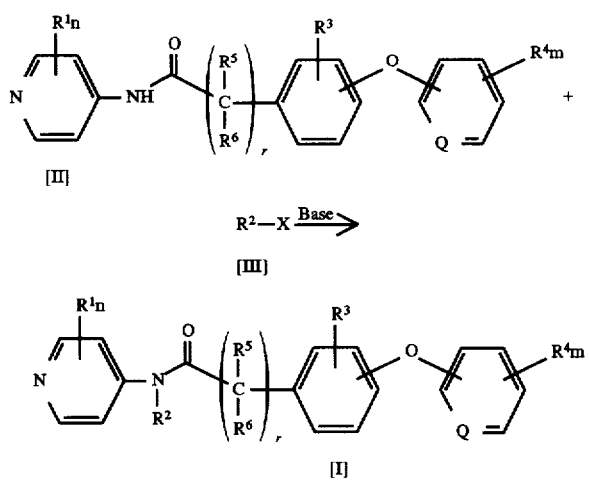

In the above formulas, X is a halogen atom, an alkoxycarbonyloxy group, an alkylsulfonyloxy group, a benzenesulfonyloxy group or a toluenesulfonyloxy group and $R^1$, $R^2$, $R^3$, $R^4$, $R^5$, $R^6$, Q, m, n and r are as defined above.

A compound of the formula (I) of the present invention can be produced by reacting a compound of the formula (II) with a compound of the formula (III) in the presence of a base.

This reaction is carried out usually in a solvent. As the solvent, any solvent can be used so long as it does not adversely affect the reaction. It may, for example, be an aromatic hydrocarbon such as benzene, toluene or xylene, an ether such as diethyl ether, tetrahydrofuran, 1,2-dimethoxyethane or 1,4-dioxane, a ketone such as acetone or methyl ethyl ketone, a nitrile such as acetonitrile or propionitrile, or an aprotic polar solvent such as dimethylsulfoxide, N,N-dimethylformamide or N,N-dimethylacetamide, or a solvent mixture in a proper combination of these solvents.

As the base, any base which is commonly used for the reaction of this type, may be used. It may, for example, be an inorganic base such as sodium carbonate, potassium carbonate, sodium hydrogen carbonate, sodium hydroxide or potassium hydroxide, an organic base such as triethylamine, pyridine, N,N-dimethylaminopyridine or 1,8-diazabicyclo[5.4.0]-7-undecene, a metal hydride such as sodium hydride or potassium hydride, or a metal alkoxide such as sodium methoxide or potassium tertbutoxide. However, the base is not limited to such specific examples.

The amounts of the respective compounds to be used are usually such that the compound of the formula (III) is from 1.0 to 5.0 mols, and the base is from 1.0 to 5.0 mols, per mol of the compound of the formula (II). The reaction temperature is an optional temperature within a range of from −50° C. to the reflux temperature in the reaction system, preferably from −30° C. to room temperature. The reaction time varies depending upon the particular compound, but can be set within a range of from 1 to 20 hours.

Process 2

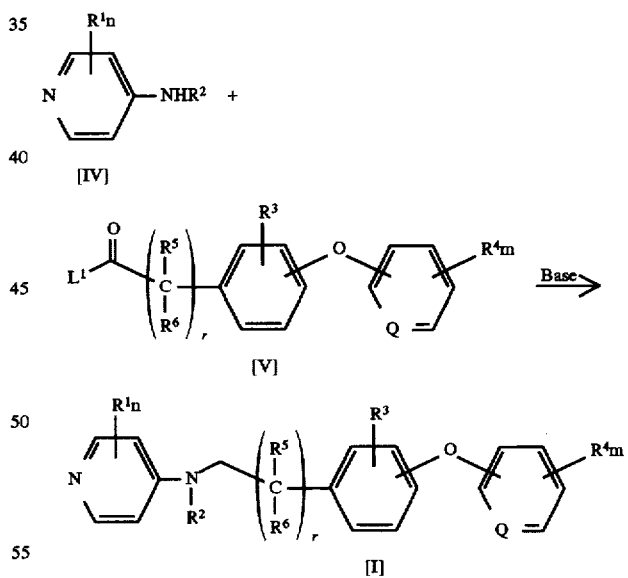

In the above formulas, $L^1$ is a halogen atom, and $R^1$, $R^2$, $R^3$, $R^4$, $R^5$, $R^6$, Q, m, n and r are as defined above.

A compound of the formula (I) of the present invention can be produced by reacting a compound of the formula (IV) with a compound of the formula (V) in the presence of a base.

This reaction can be carried out usually in a solvent. The solvent and the base which can be used here, may be the same as used in Process 1.

The amounts of the respective compounds are usually such that the compound of the formula (V) is from 1.0 to 5.0 mols, and the base is from 1.0 to 5.0 mols, per mol of the compound of the formula (IV). The reaction temperature is an optional temperature within a range of from −50° C. to the reflux temperature in the reaction system, preferably from −30° C. to room temperature. The reaction time varies depending upon the particular compound, but can be set within a range of from 1 to 20 hours.

Now, processes for producing starting material compounds to be used in the foregoing processes, will be described.

The compound of the formula (II) used as a starting material in Process 1 can be produced, for example, by the following Starting Material Production Processes A-1 to A-3.

Starting Material Production Process A-1

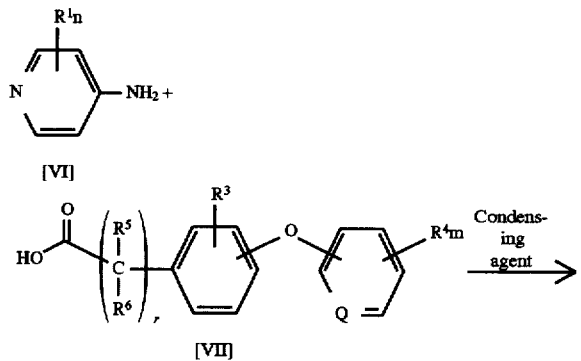

In the above formulas, $R^1$, $R^3$, $R^4$, $R^5$, $R^6$, Q, n, m and r are as defined above.

The compound of the formula (II) can be produced by reacting a compound of the formula (VI) with a compound of the formula (VII) in the presence of a condensing agent.

This reaction is carried out usually in a solvent. As the solvent, any solvent can be used so long as it does not adversely affect the reaction. It may, for example, be a halogenated hydrocarbon such as dichloromethane, chloroform or carbon tetrachloride, an aromatic hydrocarbon such as benzene, toluene or xylene, an ether such as diethyl ether, tetrahydrofuran, 1,2-dimethoxyethane or 1,4-dioxane, a ketone such as acetone or methyl ethyl ketone, a nitrile such as acetonitrile or propionitrile, or an aprotic polar solvent such as dimethylsulfoxide, N,N-dimethylformamide or N,N-dimethylacetamide or a solvent mixture in a proper combination of these solvents.

The condensing agent may, for example, be a carbodiimide such as 1,3-dicyclohexylcarbodiimide or 1-ethyl-3-(3-dimethylaminopropyl)carbodiimide hydrochloride, 1,1'-carbonyldiimidazole, diphenylphosphorylazide, 2-chloro-1-methyl-pyridinium iodide, 2-chloro-1,3-dimethylimidazolium chloride.

The amounts of the respective compounds are usually such that the compound of the formula (VII) is from 1.0 to 5.0 mols, and the condensing agent is from 1.0 to 2.0 mols, per mol of the compound of the formula (VI). The reaction temperature is an optional temperature within a range of from −50° C. to the reflux temperature in the reaction system, preferably from −10° C. to 150° C. The reaction time varies depending upon the particular compound, but can be set usually within a range of from 1 to 72 hours.

Starting Material Production Process A-2

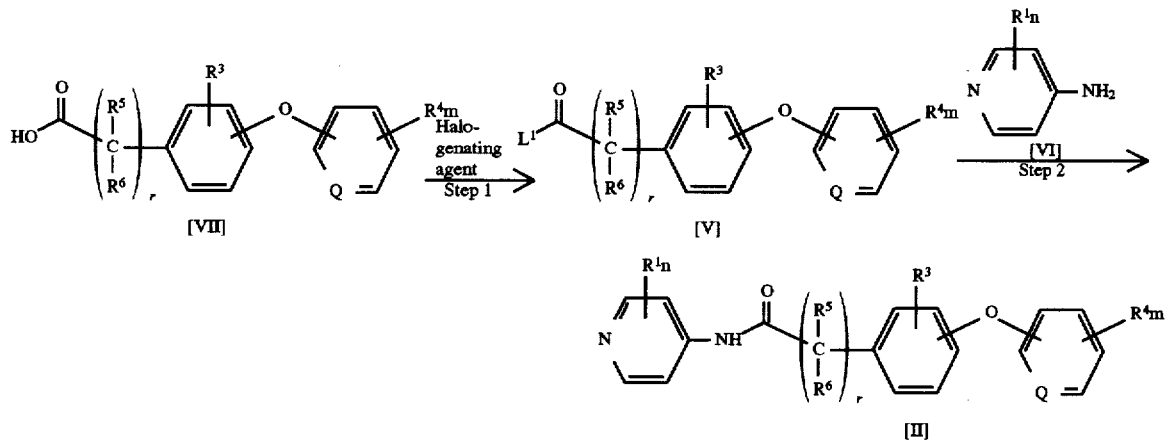

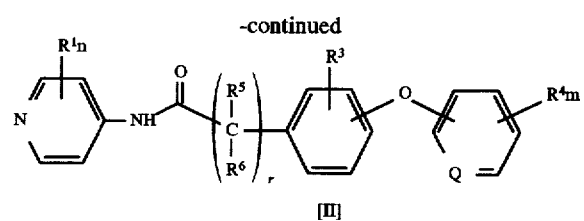

In the above formulas, $R^1$, $R^3$, $R^4$, $R^5$, $R^6$, Q, $L^1$, n, m and r are as defined above.

The starting material compound of the formula (II) can be obtained by converting a compound of the formula (VII) with a halogenating agent to a compound of the formula (V) in Step 1 and then reacting it with a compound of the formula (VI) in the presence or absence of a base in Step 2.

The reaction in Step 1 of Starting Material Production Process A-2 is carried out usually in a solvent. The solvent which can be used here, may be the same as used in Starting Material Production Process A-1.

The halogenating agent to be used may, for example, be thionyl chloride, phosphorus oxychloride, phosphorus oxybromide, phosphorus pentachloride, phosphorus pentabromide, triphenylphosphine/carbon tetrachloride or triphenylphosphine/bromine.

The amounts of the respective compounds are usually such that the halogenating agent is from 1.0 to 10.0 mols per mol of the compound of the formula (VII). The reaction temperature is an optional temperature within a range of from −50° C. to the reflux temperature in the reaction system, preferably from −10° C. to 150° C. The reaction time varies depending upon the particular compound, but can be set usually within a range of from 1 to 72 hours.

The reaction in Step 2 of Starting Material Production Process A-2 is carried out usually in a solvent. The solvent which can be used here, may be the same as used in Starting Material Production Process A-1.

The base to be used, may, for example, be an inorganic base such as sodium carbonate, potassium carbonate, sodium hydrogen carbonate, sodium hydroxide or potassium hydroxide, an organic base such as triethylamine, pyridine, N,N-dimethylaminopyridine or 1,8-diazobicyclo[5.4.0]-7-undecene, or a metal alkoxide such as sodium methoxide or potassium t-butoxide.

The amounts of the respective compounds are usually such that the compound of the formula (VI) is from 1.0 to 5.0 mols, and the base is from 1.0 to 5.0 mols, per mol of the compound of the formula (V). The reaction temperature is an optional temperature within a range of from −50° C. to the reflux temperature in the reaction system, preferably from −30° C. to 150° C. The reaction time varies depending upon the particular compound, but can be set usually within a range of from 1 to 48 hours.

Starting Material Production Process A-3 with a compound of the formula (VIII) by means of a condensing agent to obtain a compound of the formula (IX) in Step 1 and reacting it with a compound of the formula (X) in the presence of a base and in the presence or absence of a catalyst in Step 2.

The reaction in Step 1 of Starting Material Production Process A-3 is carried out usually in a solvent. The solvent and the condensing agent which can be used here, may be the same as used in Starting Material Production Process A-1.

The amounts of the respective compounds are usually such that the compound of the formula (VIII) is from 1.0 to 5.0 mols, and the condensing agent is from 1.0 to 2.0 mols, per mol of the compound of the formula (VI). The reaction temperature is an optional temperature within a range of from −50° C. to the reflux temperature in the reaction system, preferably from −10° C. to 150° C. The reaction time varies depending upon the particular compound, but can be set usually within a range of from 1 to 72 hours.

The reaction in Step 2 of Starting Material Production Process A-3 is carried out usually in a solvent. The solvent and the base which can be used here, may be the same as used in Process 1. The catalyst which can be used, may, for example, be a sulfinate such as sodium 4-toluenesulfinate, but it is not limited to such a specific example.

The amounts of the respective compounds are usually such that a compound of the formula (X) is from 1.0 to 5.0 mols, and the base is from 1.0 to 5.0 mols, per mol of the compound of the formula (IX). The reaction temperature is an optional temperature within a range of from −50° C. to the reflux temperature in the reaction system, preferably from room temperature to 150° C. The reaction time varies depending upon the particular compound, but can be set usually within a range of from 1 to 72 hours.

The compound of the formula (VII) to be used as a starting material in Starting Material Production Processes

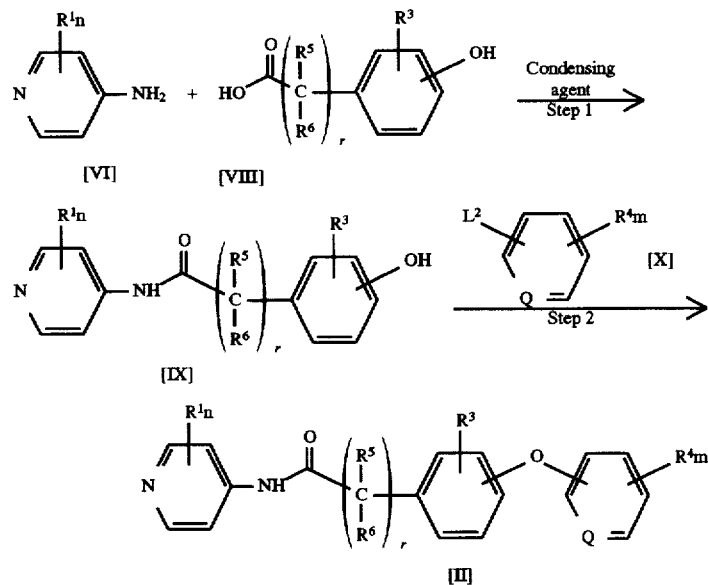

In the above formulas, $L^2$ is a halogen atom or a methane sulfonyl group, and $R^1$, $R^3$, $R^4$, $R^5$, $R^6$, Q, n, m and r are as defined above.

The starting material compound of the formula (II) can be obtained by condensing a compound of the formula (VI)

A-1 and A-2, can be produced, for example, by the following Starting Material Production Processes B-1 and B-2.

Starting Material Production Process B-1

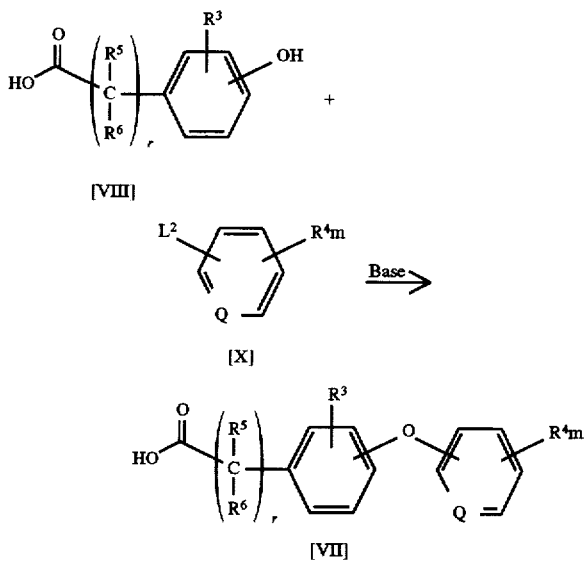

In the above formulas, $R^3$, $R^4$, $R^5$, $R^6$, Q, $L^2$, m and r are as defined above.

The compound of the formula (VII) can be produced by reacting a compound of the formula (VIII) with a compound of the formula (X) in the presence of a base and in the presence or absence of a catalyst.

This reaction is carried out usually in a solvent. The solvent and the base which can be used, may be the same as in Process 1. The catalyst which can be used here, may, for example, be a sulfinate such as sodium 4-toluenesulfinate, but the catalyst is not limited to such a specific example.

The amounts of the respective compounds are usually such that the compound of the formula (X) is from 1.0 to 5.0 mols and the base is from 2.0 to 5.0 mols, per mol of the compound of the formula (VIII). The reaction temperature is an optional temperature within a range of from room temperature to the reflux temperature in the reaction system, preferably from room temperature to 180° C. The reaction time varies depending upon the particular compound, but can be set usually within a range of from 1 to 24 hours.

Starting Material Production Process B-2

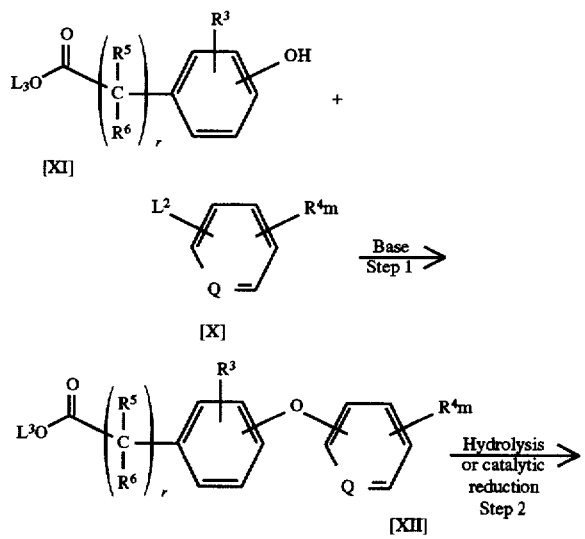

In the above formulas, $L^3$ is an alkyl group or a benzyl group, and $L^2$, $R^3$, $R^4$, $R^5$, $R^6$, Q, m and r are as defined above.

The compound of the formula (VII) can be obtained by reacting a compound of the formula (XI) with a compound of the formula (X) in the presence of a base and in the presence or absence of a catalyst to obtain a compound of the formula (XII) in Step 1 and then hydrolyzing it in Step 2 or catalytically reducing it when $R^3$ is a benzyl group.

The reaction in Step 1 of Starting Material Production Process B-2 is carried out usually in a solvent. The solvent and the base which can be used here, may be the same as in Process 1. The catalyst which can be used, may, for example, be a sulfinate such as sodium 4-toluenesulfinate, but it is not limited to such a specific example.

The amounts of the respective compounds are usually such that the compound of the formula (X) is from 1.0 to 5.0 mols, and the base is from 1.0 to 5.0 mols, per mol of the compound of the formula (XI). The reaction temperature is an optional temperature within a range of from room temperature to the reflux temperature in the reaction system, preferably from room temperature to 180° C. The reaction time varies depending upon the particular compound, but can be set usually within a range of from 1 to 24 hours.

The hydrolytic reaction in the reaction in Step 2 of Starting Material Production Process B-2 can be carried out by employing conditions which are commonly used for alkali hydrolysis or acid hydrolysis (see, for example, Shin-jikken Kagaku Kouza, Vol. 14, (II), p. 931–938). The solvent which can be used for the catalytic reduction, may, for example be an alcohol such as methanol or ethanol, an ether such as 1,2-dimethoxy ethane, tetrahydrofuran or 1,4-dioxane, or an aprotic polar solvent such as N,N-dimethylformamide or N,N-dimethylacetamide, or a solvent mixture in a proper combination of these solvents.

The compound of the formula (IV) used as the starting material in Process 2, can be produced, for example, by the following process.

Starting Material Production Process C

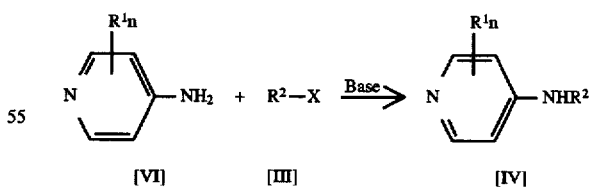

In the above formulas, $R^1$, $R^2$, X and n are as defined above.

The compound of the formula (IV) can be produced by reacting a compound of the formula (VI) with a compound of the formula (III) in the presence of a base.

This reaction is carried out usually in a solvent. The solvent and the base which can be used here, may be the same as used in Process 1.

The amounts of the respective compounds are usually such that the compound of the formula (III) is from 1.0 to 5.0 mols, and the base is from 1.0 to 5.0 mols, per mol of the compound of the formula (VI). The reaction temperature is an optional temperature within a range of from −50° C. to the reflux temperature in the reaction system, preferably from −20° C. to room temperature. The reaction time varies depending upon the particular compound, but can be set usually within a range of from 1 to 20 hours.

The 4-aminopyridine derivative of the formula (VI) can be prepared by a known method. For example, it can be prepared in the following manner with reference to e.g. J. Med. Chem., vol. 32, p. 1970–1977 (1989), J. Med. Chem., vol. 36, p. 733–746 (1993) and J. Med. Chem., vol. 33, p. 2231–2239 (1989).

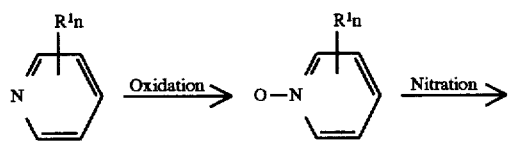

Further, the monochloro-substituted 4-aminopyridine is disclosed in Beilstein, vol. 22, IV, P. 4118. However, it can be produced also by the following method.

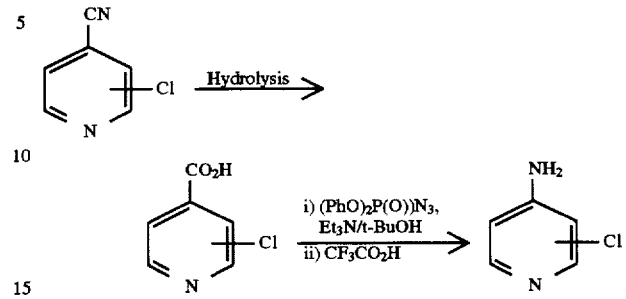

Namely, 4-amino-2-chloropyridine and 4-amino-3-chloropyridine can be obtained by separating by column chromatography a mixture of 3-chlro-4-cyanopyridine and 2-chloro-4-cyanopyridine, synthesized by the method disclosed in J. Heterocyclic. Chem. , vol. 15, p. 683–684 (1978), hydrolyzing the respective compounds under an alkaline condition or an acidic condition to obtain carboxylic acid derivatives, which are subjected to Curtius rearrangement and then treated with trifluoroacetic acid.

2,3-dichloro-4-aminopyridine and 2,5-dichloro-4-aminiopyridine are disclosed in Beilstein, vol. 22, IV, p. 4118. However, it can be produced also by the following method.

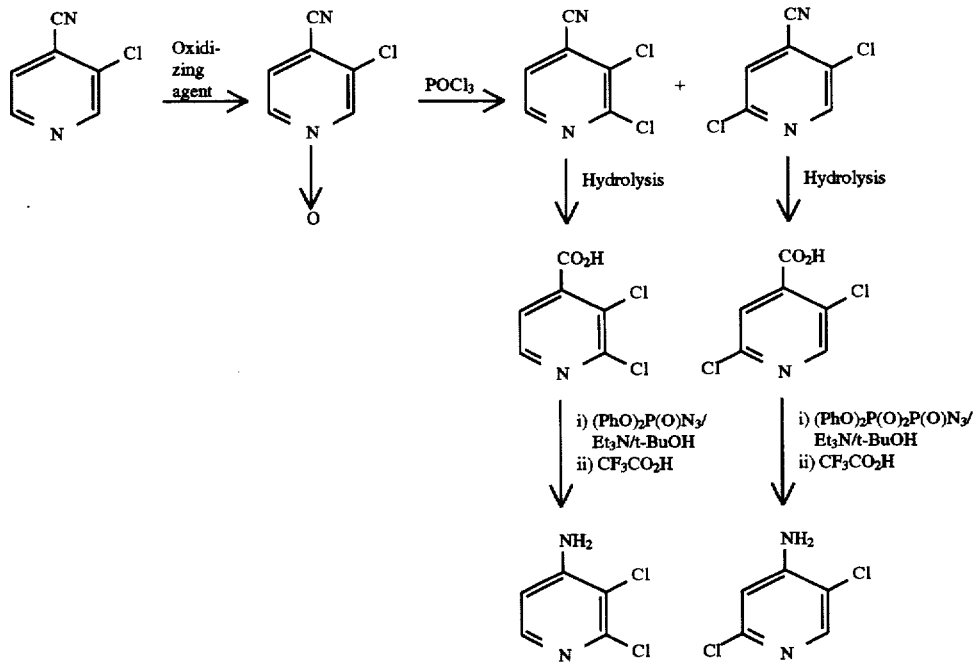

3-chloro-4-cyanopyridine is converted to N-oxide by means of an oxidizing agent such as hydrogen peroxide or m-chloroperbenzoate, and phosphorus oxychloride is reacted thereto to obtain 4-cyano-2,3-dichloropyridine and 4-cyano-2,5-dichloropyridine. These compounds can be separated by column chromatography. The separated compounds are respectively hydrolyzed under an alkaline condition or an acidic condition to obtain the respective carboxylic acids, which are then subjected to Curtius rearrangement and then treated with trifluoroacetic acid to

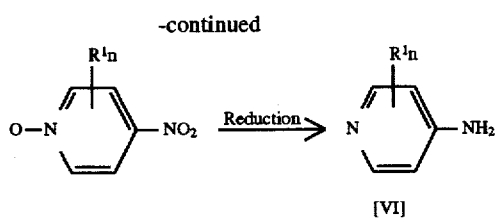

obtain 4-amino-2,3-dichloro-pyridine and 4-amino-2,5-dichloropyridine.

BEST MODE FOR CARRYING OUT THE INVENTION

Now, the present invention will be described in further detail with reference to Preparation Examples, Formulation Examples and Test Examples.

PREPARATION EXAMPLE 1

Preparation of N-(3-chloro-2-ethylpyridin-4-yl)-N-methoxycarbonyl-4-[(5-trifluoromethylpyridin-2-yl)oxy]phenylacetamide (Compound No. I-118)

0.87 g (2.0 mmol) of N-(3-chloro-2-ethylpyridin-4-yl)-4-[(5-trifluoromethylpyridin-2-yl)oxy]phenylacetamide was dissolved in 5 ml of tetrahydrofuran, and the solution was stirred at room temperature. Then, 0.058 g (2.4 mmol) of sodium hydride was gradually added thereto, and the mixture was further stirred for one hour at room temperature. Then, 2 ml of a tetrahydrofuran solution containing 0.38 g (4.0 mmol) of methyl chloroformate was dropwise added thereto at a temperature of from −5° to 0° C, and the mixture was stirred for 30 minutes at a temperature of from −5° to 0° C. and for 12 hours at room temperature. Then, the reaction solution was poured into ice water and extracted with ethyl acetate. The organic layer was washed with water and then dried over anhydrous magnesium sulfate. Then, ethyl acetate was distilled off under reduced pressure. The obtained residue was purified by silica gel column chromatography (developing solvent: n-hexane/ethyl acetate) and then purified by high performance liquid chromatography to obtain 0.28 g of the desired product as a white powder (melting point: 62° to 64° C.)

$^1$H-NMR data (60 MHz, CDCl$_3$ solvent, δ value, ppm)

| | |
|---|---|
| 8.57–8.37 | (2H, m) |
| 7.90 | (1H, dd) |
| 7.57–6.87 | (6H, m) |
| 4.43 | (2H, s) |
| 3.75 | (3H, s) |
| 3.02 | (2H, q) |
| 1.33 | (3H, t) |

PREPARATION EXAMPLE 2

Preparation of N-(3-chloro-2-ethylpyridin-4-yl)-N-isobutyloxycarbonyl-4-[(5-trifluoromethylpyridin-2-yl)oxy]phenylacetamide (Compound No. I-49)

1.0 g (2.3 mmol) of N-(3-chloro-2-ethylpyridin-4-yl)-4-[(5-trifluoromethylpyridin-2-yl)oxy]phenylacetamide was dissolved in 5 ml of dimethoxy ethane, and the solution was stirred at room temperature. Then, 0.067 g (2.8 mmol) of sodium hydride was gradually added thereto, and the mixture was further stirred for one hour at room temperature. Then, 2 ml of a 1,2-dimethoxyethane solution containing 0.38 g (2.8 mmol) of isobutyl chloroformate was dropwise added thereto at a temperature of from −5° to 0° C., and the mixture was stirred for 30 minutes at a temperature of from −5° to 0° C. and for one hour at room temperature. Then, the reaction solution was poured into ice water and extracted with ethyl acetate. The organic layer was washed with water and then dried over anhydrous magnesium sulfate. Then, ethyl acetate was distilled off under reduced pressure. The obtained residue was purified by silica gel column chromatography (developing solvent: n-hexane/ethyl acetate) to obtain 0.4 g of the desired product as a yellow viscous substance (refractive index n$_D$$^{20}$=1.3582).

$^1$H-NMR data (60 MHz, CDCl$_3$ solvent, δ value, ppm)

| | |
|---|---|
| 8.46–8.31 | (2H, m) |
| 7.83 | (1H, dd) |
| 7.49–7.16 | (6H, m) |
| 4.42 | (2H, d) |
| 3.90 | (2H, d) |
| 3.08 | (2H, q) |
| 2.04–1.53 | (1H, m) |
| 1.30 | (3H, t) |
| 0.72 | (6H, d) |

PREPARATION EXAMPLE 3

Preparation of N-(3-chloro-2-ethylpyridin-4-yl)-N-propargyl-4-[(5-trifluoromethylpyridin-2-yl)oxy]phenylacetamide (Compound No. I-95)

1.0 g (2.3 mmol) of N-(3-chloro-2-ethylpyridin-4-yl)-4-[(5-trifluoromethylpyridin-2-yl)oxy]phenylacetamide was dissolved in 5 ml of N,N-dimethylacetamide, and the solution was stirred at room temperature. Then, 0.067 g (2.8 mmol) of sodium hydride was gradually added thereto, and the mixture was further stirred for one hour at room temperature. Then, 10.3 (2.5 mmol) of propargyl bromide was added thereto, and the mixture was stirred for one hour at room temperature. Then, 0.3 g (2.5 mmol) of propargyl bromide was further added thereto, and the mixture was stirred for one hour at a temperature of from 50° to 60° C. Then, the reaction solution was poured into ice water and extracted with ethyl acetate. The organic layer was washed with water and then dried over anhydrous magnesium sulfate. Then, ethyl acetate was distilled off under reduced pressure. The obtained residue was purified by silica gel column chromatography (developing solvent: n-hexane/ethyl acetate) and then purified by high performance liquid chromatography to obtain 0.5 g of the desired product as a brown viscous substance (refractive index n$_D$$^{20}$=1.35619).

$^1$H-NMR data (60 MHz, CDCl$_3$ solvent, δ value, ppm)

| | |
|---|---|
| 8.49 | (1H, d) |
| 8.45–8.35 | (1H, m) |
| 7.87 | (1H, dd) |
| 7.33–6.85 | (6H, m) |
| 5.35 | (1H, dd) |
| 3.95 | (1H, dd) |
| 3.43 | (2H, s) |
| 3.05 | (2H, q) |
| 2.22 | (1H, t) |
| 1.35 | (3H, t) |

PREPARATION EXAMPLE 4

Preparation of N-(3-chloro-2-ethylpyridin-4-yl)-N-methoxycarbonyl-4-[(5-trifluoromethylpyridin-2-yl)oxy]phenylacetamide (Compound No. I-118)

2.0 g (9.3 mmol) of methyl N-(3-chloro-2-ethylpyridin-4-yl)-carbamate was dissolved in 10 ml of N,N-dimethylacetamide, and the solution was stirred at room temperature. Then, 0.27 g (11.2 mmol) of sodium hydride was gradually added thereto, and the mixture was stirred for one hour at room temperature. Then, 5.5 g (17.4 mmol) of 4-[(5-trifluoromethylpyridin-2-yl)oxy]phenylacetyl chloride was dropwise added thereto at −15° C., and the mixture was stirred for 3 hours at a temperature of from −15° to −10° C. Then, the reaction solution was poured into a sodium hydrogen carbonate solution cooled with ice and extracted with ethyl acetate. The organic layer was washed with water and then dried over anhydrous magnesium sulfate. Then, ethyl acetate was distilled off under reduced pressure. The obtained residue was purified by silica gel column chromatography (developing solvent: n-hexane/ethyl acetate) and further purified by a thin layer chromatography to obtain 1.2 g of the desired product as a white powder (melting point: 62° to 64° C.).

REFERENCE EXAMPLE 1

Preparation of N-(2-chloropyridin-4-yl)-4-[(5-trifluoromethylpyridin-2-yl)oxy]phenylacetamide (Intermediate No. 5)

2.3 g (7.78 mmol) of 4-[(5-trifluoromethylpyridin-2-yl)oxy]phenylacetic acid was dissolved in 10 ml of dichloromethane and cooled to a temperature of from −10° to 0° C. Then, 1.94 g (10.1 mmol) of 1-ethyl3-(dimethylaminopropyl)carbodiimide hydrochloride was added thereto, and the mixture was stirred at a temperature of from −10° to 0° C. 20 minutes later, 1.0 g (7.78 mmol) of 4-amino-2-chloropyridine was added thereto, and the mixture was gradually returned to room temperature with stirring and further stirred over night at room temperature. Then, 10 ml of dichloromethane was added to the reaction solution. The organic layer was washed with water and then dried over anhydrous magnesium sulfate. Then, dichloromethane was distilled off under reduced pressure. The obtained residue was purified by silica gel column chromatography (developing solvent: n-hexane/ethyl acetate) to obtain 2.3 g of the desired product as a slightly yellow powder (melting point: 49 to 53° C.).

$^1$H-NMR data (60 MHz, CDCl$_3$ solvent, δ value, ppm)

| 9.10 | (1H, bs) |
| 8.37 | (1H, d) |
| 8.16 | (1H, d) |
| 7.88 | (1H, q) |
| 7.65 | (1H, d) |
| 7.20 | (4H, m) |
| 6.98 | (1H, d) |
| 3.73 | (2H, s) |

REFERENCE EXAMPLE 2

Preparation of N-(3-chloro-2-ethylpyridin-4-yl)-4-[(5-trifluoromethylpyridin-2-yl)oxy]phenylacetamide (Intermediate No. 12)

3.6 g (12.1 mmol) of 4-[(5-trifluoromethylpyridin-2-yl)oxy]phenylacetic acid was dissolved in 20 ml of 4dioxane, and the solution was stirred at room temperature. Then, 2.4 g (14.8 mmol) of 1,1′-carbonyldiimidazole was gradually added thereto, and the mixture was stirred for one hour at room temperature. Then, 1.8 g (11.5 mmol) of 4-amino-3-chloro-2-ethylpyridine was added thereto, and the mixture was refluxed under heating for 30 minutes. The reaction solution was concentrated, and the residue was extracted with ethyl acetate. The organic layer was washed with water and then dried over anhydrous magnesium sulfate. Then, ethyl acetate was distilled off under reduced pressure. The obtained residue was purified by silica gel column chromatography (developing solvent: n-hexane/ethyl acetate) to obtain 3.0 g of the desired product as colorless cotton-like crystals (melting point: 124.5° to 125° C.).

$^1$H-NMR data (60 MHz, CDCl$_3$ solvent, δ value, ppm)

| 8.38 | (1H, d) |
| 8.31 | (1H, d) |
| 8.18 | (1H, d) |
| 7.90 | (1H, bs) |
| 7.88 | (1H, q) |
| 7.53–7.07 | (4H, m) |
| 7.02 | (1H, d) |
| 3.83 | (2H, s) |
| 2.89 | (2H, q) |
| 1.27 | (3H, t) |

REFERENCE EXAMPLE 3

Preparation of N-(3-chloro-2-ethylpyridin-4-yl)-4-[(5-trifluoromethylpyridin-2-yl)oxy]phenylacetamide (Intermediate No. 12)

2.97 g (10.0 mmol) of 4-[(5-trifluoromethylpyridin-2-yl)oxy]phenylacetic acid was dissolved in 20 ml of dichloromethane, and the solution was cooled to a temperature of from −10° to 0° C. Then, 2.30 g (12.0 mmol) of 1-ethyl-3-(3-dimethylaminopropyl)carbodiimide hydrochloride was added thereto, and the mixture was stirred at a temperature of from −10° to 0° C. 30 minutes later, 1.57 g (10.0 mmol) of 4-amino-3-chloro-2-ethylpyridine was added thereto, and the mixture was gradually returned to room temperature with stirring and further stirred for 16 hours at room temperature. Then, 10 ml of dichloromethane was added to the reaction solution. The organic layer was washed with water and then dried over anhydrous magnesium sulfate. Then, dichloromethane was distilled off under reduced pressure. The obtained residue was purified by silica gel column chromatography (developing solvent: n-hexane/ethyl acetate) to obtain 1.14 g of the desired product as colorless cotton-like crystals (melting point: 124.5° to 125° C.).

REFERENCE EXAMPLE 4

Preparation of N-(3-chloro-2-ethylpyridin-4-yl)-4-hydroxyphenylacetamide 0.76 g (5.0 mmol) of 4-hydroxyphenyl acetic acid was dissolved in 20 ml of 1,4-dioxane, and the solution was stirred at 5° C. Then, 0.97 g (6.0 mmol) of 1,1′-carbonyldiimidazole was added thereto, and the mixture was stirred for one hour at 5° C. Then, 0.76 g (5.0 mmol) of 4-amino-3-chloro-2-ethylpyridine was added thereto, and the mixture was refluxed under heating for 20 hours. The reaction solution was poured into water and extracted with ethyl acetate. The organic layer was washed with water and then dried over anhydrous magnesium sulfate. Then, ethyl acetate was distilled off under reduced pressure. The obtained residue was purified by silica gel column chromatography (developing solvent: n-hexane/ethyl acetate) and then recrystallized from ethanol to obtain 0.7 g of the desired product as a white powder (melting point: 158° to 161° C.).

REFERENCE EXAMPLE 5

Preparation of N-(3-chloro-2-ethyl-pyridin-4-yl)-4-[(5-nitropyridin-2-yl)oxy]phenylacetamide (Intermediate No. 16)

0.59 g (2 mmol) of N-(3-chloro-2-ethylpyridin-4-yl)-4-hydroxyphenylacetamide, 0.32 g (2.2 mmol) of potassium carbonate, 0.35 g (2.2 mmol) of 2-chloro-5-nitropyridine and 0.01 g of sodium 4-toluenesulfinate were dissolved in 5 ml of N,N-dimethylformamide, and the solution was stirred for 50 minutes at 80° C. After completion of the reaction, the reaction solution was poured into water and extracted twice with ethyl acetate. The organic layer was washed with water and then dried over anhydrous magnesium sulfate. Then, ethyl acetate was distilled off under reduced pressure. The obtained residue was purified by silica gel column chromatography (developing solvent: n-hexane/ethyl acetate) to obtain 0.5 g of the desired product as a milky white powder (melting point: 128° to 131° C.).

$^1$H-NMR data (60 MHz, CDCl$_3$ solvent, δ value, ppm)

| | |
|---|---|
| 8.99 | (1H, d) |
| 8.40 | (1H, q) |
| 8.20 | (2H, d) |
| 7.87 | (1H, bs) |
| 7.01–7.47 | (5H, m) |
| 3.80 | (2H, s) |
| 2.90 | (2H, q) |

REFERENCE EXAMPLE 6-1

Preparation of 3-chloro-4-[(5-trifluoromethylpyridin-2-yl)oxy]phenylacetic acid 9.3 g (50 mmol) of 3-chloro-4-hydroxylphenylacetic acid was dissolved in 100 ml of N,N-dimethylformamide, and 15.2 g (110 mmol) of potassium carbonate was added thereto. The mixture was stirred at 100° C. for one hour. Then, 10.9 g (60 mmol) of 2-chloro-5-trifluoromethylpyridine was added thereto, and the mixture was stirred for 8 hours at 120° C. After cooling, the reaction solution was poured into water and washed twice with ethyl acetate. The obtained aqueous layer was adjusted to pH 4 with citric acid and extracted with ethyl acetate. The organic layer was dried over anhydrous magnesium sulfate. Then, ethyl acetate was distilled off under reduced pressure. The obtained residue was recrystallized from ethanol to obtain 8.3 g of the desired product as a white powder (melting point: 138° to 139° C.).

REFERENCE EXAMPLE 6-2

Preparation of 4-((5-trifluoromethylpyridin-2-yl)oxy]phenylacetic acid 49.9 g (300 mmol) of methyl 4-hydroxyphenyl acetate was dissolved in 300ml of N,N-dimethylformamide. Then, 45.6 g (330 mmol) of potassium carbonate was added thereto, and the mixture was stirred for one hour at 120° C. Further, 59.9 g (330 mmol) of 2-chloro-5-trifluoromethylpyridine was added thereto, and the mixture was stirred for two hours at 120° C. After cooling, the reaction solution was poured into water and extracted with ethyl acetate. The organic layer was washed with a 5% sodium hydroxide aqueous solution and then with water, and then dried over anhydrous magnesium sulfate. Then, ethyl acetate was distilled off under reduced pressure. The obtained residue was purified by silica gel column chromatography (developing solvent: n-hexane/ethyl acetate) to obtain 69.1 g of a colorless viscous substance. Then, 250 ml of methanol and 30 ml of an aqueous solution containing 9.8 g of sodium hydroxide were added thereto, and the mixture was stirred for 12 hours at room temperature. The reaction solution was concentrated, and water was added thereto. The mixture was washed with chloroform, and the obtained aqueous layer was adjusted to pH 4 with citric acid and extracted with chloroform. The organic layer was dried over anhydrous magnesium sulfate. Then, chloroform was distilled off under reduced pressure to obtain 57.4 g of the desired product as a white powder (melting point: 100° to 102° C.).

REFERENCE EXAMPLE 6-3

Preparation of 4-[(5-cyanopyridin-2-yl)oxy] phenylacetic acid 24.2 g of (100 mmol) of benzyl 4-hydroxyphenyl acetate was dissolved in 100 ml of N,N-dimethylformamide. Then, 15.2 (110 mmol) of potassium carbonate was added thereto, and the mixture was stirred for one hour at 120° C. Further, 14.9 g (110 mmol) of 2-chloro-5-cyanopyridine was added thereto, and the mixture was stirred for 6 hours at 120° C. After cooling, the reaction solution was poured into water and extracted with ethyl acetate. The organic layer was washed sequentially with a 5% sodium hydroxide aqueous solution and water and then dried over anhydrous magnesium sulfate. Then, ethyl acetate was distilled off under reduced pressure. The obtained residue was recrystallized from ethanol to obtain 19.4 g of benzyl 4-(5-cyanopyridine-2-yl)oxyphenylacetate (melting point: 96° to 97° C.).

Then, 250 ml of ethanol and 5% palladium carbon were added thereto, followed by catalytic reduction under atmospheric pressure. After completion of the reaction, 5% palladium carbon was filtered off, and the filtrate was concentrated to obtain 2.0 g of the desired product as a white powder (melting point: 148° to 151° C.). Further, the 5% palladium carbon separated y filtration was extracted with chloroform, and the chloroform layer was concentrated to obtain 3.0 g of the desired product.

REFERENCE EXAMPLE 7

Preparation of N-(pyridin-4-yl)-4-[(5-trifluoromethylpyridin-2-yl)oxy]phenylacetamide (Intermediate No. 1)

3.0 g (10.1 mmol) of 4-[(5-trifluoromethylpyridin-2-yl) oxy]phenylacetic acid was dissolved in 15 ml of benzene. Then, 1.8 g (15.1 mmol) of thionyl chloride was added thereto, and the mixture was refluxed under heating for 1.5 hours. Then, benzene and thionyl chloride were distilled off under reduced pressure. To the obtained residue, 15 ml of acetonitrile, 0.95 g (10.1 mmol) of 4-aminopyridine and 1.2 g (11.8 mmol) of triethylamine were added, and the mixture was refluxed under heating for 8 hours. After cooling, the reaction solution was poured into water and extracted with ethyl acetate. The organic layer was washed with water and then dried over anhydrous magnesium sulfate. Then, ethyl acetate was distilled off under reduced pressure. The obtained residue was purified by silica gel column chromatography (developing solvent: n-hexane/ethyl acetate) to obtain 0.45 g of the desired product as a milky white powder (melting point: 167.0° to 170.0° C.).

$^1$H-NMR data (60 MHz, CDCl$_3$ solvent, δ value, ppm)

| | |
|---|---|
| 8.57–8.10 | (4H, m) |
| 7.87 | (1H, q) |
| 7.57–6.87 | (7H, m) |
| 3.72 | (2H, s) |

REFERENCE EXAMPLE 8

Preparation of 4-cyano-2,5-dichloropyridine and 4-cyano-2,3-dichloropyridine 9.6 g of 3-chloro-4-cyanopyridine was dissolved in 70 ml of dichloromethane. Then, 23.2 g of a 31% hydrogen peroxide aqueous solution and 16.0 g of trifluoroacetic acid were added thereto, and the mixture was stirred overnight at room temperature. After completion of the reaction, the reaction solution was extracted with dichloromethane. The organic layer was washed sequentially with an aqueous sodium hydrogen carbonate solution and an aqueous sodium hydrogen sulfite solution and the dried over anhydrous magnesium sulfate. Then, dichloromethane was distilled off under reduced pressure. The obtained residue was washed with isopropyl ether to obtain 7.2 g of 3-chloro-4-cyanopyridine N-oxide as a white powder (melting point: 172° to 174° C.). Then, 20 ml of phosphorus oxychloride was added to this 3-chloro-4-cyanopyridine N-oxide, and the mixture was refluxed under heating for 5 hours. After cooling, the reaction solution was gradually poured into an aqueous sodium hydrogen carbonate solution and extracted with ethyl acetate. The organic layer was washed with water and then dried over anhydrous magnesium sulfate. Then, ethyl acetate was distilled off under reduced pressure. The obtained residue was purified by silica gel column chromatography (developing solvent: n-hexane/ethyl acetate) to obtain 3.2 g of 4-cyano-2,5-dichloropyridine (melting point: 55° to 58° C.) and 2.5 g of 4-cyano-2,3-dichloropyridine (melting point: 65° to 69° C.).

REFERENCE EXAMPLE 9

Preparation of 4-amino-2,3-dichloropyridine 40 ml of concentrated hydrochloric acid was added to 4.0 g of 4-cyano-2,3-dichloropyridine, and the mixture was refluxed under heating for 8 hours. Water was distilled off, and then 10 ml of water was added thereto. The mixture was adjusted to pH=1 to 2 with sodium hydrogen carbonate, whereupon the precipitated crystals were collected by filtration. The crystals were washed with water and dried to obtain 2.3 g of 2,3-dichloroisonicotinic acid as a white powder. Then, 3.5 g of diphenylphosphorylazide, 1.3 g of triethylamine and 30 ml of -butanol were added thereto, and the mixture was refluxed under heating for 6 hours. After cooling, the mixture was poured into water and extracted with ethyl acetate. The organic layer was washed with water and then dried over anhydrous magnesium sulfate. Then, ethyl acetate was distilled off under reduced pressure. To the residue, 20 ml of trifluoroacetic acid was added, and the mixture was stirred for 2 hours at room temperature. Then, trifluoroacetic acid was distilled off under reduced pressure, and then ethyl acetate was added. The mixture was washed sequentially with an aqueous sodium hydrogen carbonate solution and an aqueous sodium chloride solution and then dried over anhydrous magnesium sulfate. Then, ethyl acetate was distilled off under reduced pressure. The obtained solid was washed with a mixture of isopropyl ether and n-hexane to obtain 1.3 g of the desired product as a white powder (melting point: 146° to 148° C.).

REFERENCE EXAMPLE 10

Preparation of methyl N-(3-chloro-2-ethylpyridin-4-yl)carbamate 5.7 g (36.4 mmol) of 4-amino-3-chloro-2-ethylpyridine was dissolved in 50 ml of methyl ethyl ketone. Then, 5.5 g (54.6 mmol) of triethylamine was added thereto, and the mixture was stirred at −10° C. Then, 8.6 g (91.0 mmol) of methyl chloroformate was gradually added thereto so that the temperature would not exceed −5° C. After completion of the dropwise addition, the mixture was stirred for one hour at a temperature of from −10° to −5° C. and for further one hour at room temperature. Then, the reaction solution was poured into water and extracted with ethyl acetate. The organic layer was washed with water and then dried over anhydrous magnesium sulfate. Then, ethyl acetate was distilled off under reduced pressure. The obtained residue was recrystallized from isopropyl ether to obtain 5.0 g of the desired product as colorless prism crystals (melting point: 78° to 79° C.).

$^1$H-NMR data (60 MHz, CDCl$_3$ solvent, δ value, ppm)

| | |
|---|---|
| 8.25 | (1H, d) |
| 7.92 | (1H, d) |
| 7.33 | (1H, bs) |
| 3.78 | (3H, s) |
| 2.92 | (2H, q) |
| 1.27 | (3H, t) |

Among Intermediates (II) and (IX), specific examples of novel compounds are shown in Tables 18 to 20.

TABLE 18

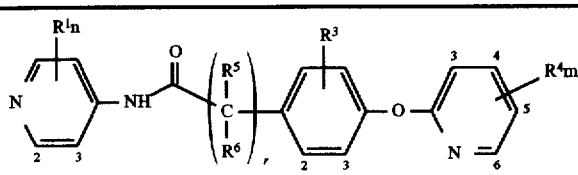

| Intermediate No. | R$^1$n | R$^3$ | R$^4$m | R$^5$ | R$^6$ | r | m.p. (°C.) or refractive index (n$_D^{20}$) |
|---|---|---|---|---|---|---|---|
| 1 | H | H | 5-CF$_3$ | H | H | 1 | 167–170 |
| 2 | H | H | 5-CF$_3$ | Pr-i | H | 1 | 101–105 |
| 3 | H | H | 3-Cl, 5-CF$_3$ | H | H | 1 | 160–163 |
| 4 | H | 3-Cl | 5-CF$_3$ | H | H | 1 | 71–74 |
| 5 | 2-Cl | H | 5-CF$_3$ | H | H | 1 | 49–53 |
| 6 | 3-Cl | H | 5-CF$_3$ | H | H | 1 | 1.5762 |
| 7 | 2, 3-Cl$_2$ | H | 5-CF$_3$ | H | H | 1 | 1.5865 |
| 8 | 2, 5-Cl$_2$ | H | 5-CF$_3$ | H | H | 1 | 1.5680 |
| 9 | 2-Et | H | 5-CF$_3$ | H | H | 1 | 1.5705 |
| 10 | 2-Et, 3-Cl | H | 5-Cl | H | H | 1 | 97–99 |
| 11 | 2-Et, 3-Cl | H | 5-Br | H | H | 1 | 97–100 |
| 12 | 2-Et, 3-Cl | H | 5-CF$_3$ | H | H | 1 | 124.5–125 |
| 13 | 2-Et, 3-Cl | H | 5-CF$_3$ | H | H | 2 | 141–142.5 |

TABLE 18-continued

[Structure: pyridine-NH-C(=O)-(CR5R6)r-phenyl(R3)-O-pyridine(R4m), with R1n on first pyridine]

| Intermediate No. | R¹n | R³ | R⁴m | R⁵ | R⁶ | r | m.p. (°C.) or refractive index ($n_D^{20}$) |
|---|---|---|---|---|---|---|---|
| 14 | 2-Et, 3-Cl | H | 5-CF₃ | H | H | 3 | 78–80 |
| 15 | 2-Et, 3-Cl | H | 5-CF₃ | H | H | 4 | |
| 16 | 2-Et, 3-Cl | H | 5-NO₂ | H | H | 1 | 128–131 |
| 17 | 2-Et, 3-Cl | H | 5-CN | H | H | 1 | 131–131.5 |
| 18 | 2-Et, 3-Cl | H | 3-Cl, 5-CF₃ | H | H | 1 | 136.5–139.5 |
| 19 | 2-Et, 3-Cl | H | 5-COOEt | H | H | 1 | 82–83 |
| 20 | 2-Et, 3-Cl | H | 5-COOC₂H₄Si(Me)₃ | H | H | 1 | 77–79 |
| 21 | 2-Et, 3-Cl | 3-F | 5-CF₃ | H | H | 1 | 101–102 |
| 22 | 2-Et, 3-Cl | 3-Cl | 5-CF₃ | H | H | 1 | 117–119 |
| 23 | 2-Et, 3-Cl | 3-OMe | 5-CF₃ | H | H | 1 | 1.5651 |
| 24 | 2-Et, 3-Br | H | 5-CF₃ | H | H | 1 | |

TABLE 19

| Intermediate No. | Structure | m.p. (°C.) or refractive index ($n_D^{20}$) |
|---|---|---|
| 25 | [Et, Cl-substituted pyridine-NH-C(=O)-CH₂-phenyl-O-pyridine with NC substituent] | 144–148 |
| 26 | [Et, Cl-substituted pyridine-NH-C(=O)-CH₂-phenyl-O-pyridine] | 1.6180 |
| 27 | [Et, Cl-substituted pyridine-NH-C(=O)-CH₂-phenyl-O-pyridine-CF₃] | 77.5–79.5 |

TABLE 20

[Structure: pyridine(R1n)-NH-C(=O)-(CR5R6)r-phenyl(R3)-OH]

| Intermediate No. | R¹n | R³ | R⁵ | R⁶ | r | m.p. (°C.) or refractive index ($n_D^{20}$) |
|---|---|---|---|---|---|---|
| 28 | H | H | H | H | 1 | 233–237 |
| 29 | H | H | Pr-i | H | 1 | 234–236 |
| 30 | H | 3-Cl | H | H | 1 | 228–231 |
| 31 | 2-Et, 3-Cl | H | H | H | 1 | 155–158 |

When the compound of the present invention is to be used as the active component of a pesticide, it may be used by itself. However, it can be formulated into various formulations such as an emulsifiable concentrate, a suspension, a dust, a granule, a tablet, a wettable powder, a water-soluble concentrate, a solution, a flowable suspension, a water dispersible granule, an aerosol, a paste, an oil formulation, a concentrated emulsion in water in combination with various carriers, surfactants and other adjuvants which are commonly used for formulation as agricultural adjuvants. They are blended usually in such proportions that the active ingredient is from 0.1 to 90 parts by weight and the agricultural adjuvants are from 10 to 99.9 parts by weight.

The carriers to be used for such formulation may be classified into solid carriers and liquid carriers. The solid carriers include, for example, animal and plant powders such as starch, active carbon, soybean powder, wheat powder, wood powder, fish powder and powdered milk, and mineral powders such as talc, kaolin, bentonite, calcium carbonate, zeolite, diatomaceous earth, fine silica powder, clay and alumina. The liquid carries include, for example, water, alcohols such as isopropyl alcohol and ethylene glycol, ketones such as cyclohexanone and methyl ethyl ketone, ethers such as dioxane and tetrahydrofuran, aliphatic hydrocarbons such as kerosene and light oil, aromatic hydrocarbons such as xylene, trimethylbenzene, tetramethylbenzene, methylnaphthalene and solvent naphtha, halogenated hydrocarbons such as chlorobenzene, acid amides such as dimethylacetamide, esters such as glycerin esters of fatty acids, nitriles such as acetonitrile, and sulfur-containing compounds such as dimethylsulfoxide.

The surfactants include, for example, metal salts of alkylbenzene sulfonic acids, metal salts of dinaphthylmethanedisulfonic acid, alcohol sulfuric acid esters, alkylarylsulfonates, lignin sulfonates, polyoxyethylene glycol ethers, polyoxyethylene alkyl aryl ethers and polyoxyethylene sorbitan monoalkylates.

Others adjuvants include, for example, an adhesive or thickener such as carboxymethylcellulose, gum arabic, sodium arignate, guar gum, tragacanth gum or polyvinyl alcohol, an antifoaming agent such as metal soap, a physical property-improving agent such as a fatty acid, an alkyl phosphate, silicone or paraffin, and a coloring agent.

When these formulations are to be practically used, they may be used as they are or as diluted with a diluting agent such as water to a predetermined concentration. Various formulations containing the compounds of the present invention or their diluted solutions may be applied by conventional methods i.e. application methods (such as spraying, misting, atomizing, dusting, granule application, paddy water application or seeding box treatment), soil treatment (such as mixing or drenching), surface application (such as painting, dressing or covering), dipping or poison bait. Further, the above active component may be fed as mixed in feeds to domestic animals, so that infestation or growth of pests, particularly injurious insects can be prevented by the excrements. Otherwise, it can also be applied by a so-called super high concentration low volume application method, whereby the active component may be contained up to 100%.

The pesticide of the present invention is applied usually in a concentration of the active ingredient of from 0.1 to 50,000 ppm, preferably from 1 to 10,000 ppm.

The concentration of the active ingredient can be suitably changed depending upon the type of the formulation, the method, the purpose, the season or the site of application and the state of infestation of pests. For example, in the case of aquatic pests, they can be controlled by applying a formulation having a concentration within the above mentioned range to the infested site, and therefore, the range of the active ingredient in water is lower than the above range. The dose per unit area is usually from 0.1 to 5,000 g, preferably from 1 to 1,000 g, per 1 ha of the active compound. However, the dose is not limited to such a specific range.

The compound of the present invention is sufficiently effective when used alone. However, as a case requires, it may be used in combination or in admixture with fertilizers or other agricultural chemicals such as insecticides, acaricides, nematicides, fungicides, antivirus agents, attractants, herbicides or plant growth regulants, and further improved effects may sometimes be obtained by such combined use.

Typical examples of the insecticides, fungicides and acaricides which can be used in combination with the compound of the present invention, will be given below.

Organophosphorus compounds and carbamate insecticides: fenthion, fenitrothion, diazinon, chlorpyriphos, oxydeprofos, vamidothion, phenthoate (fentoat), dimethoate, formothion, malathion, trichlorphon, thiometon, phosmet, dichlorvos, acephate, EPBP (0-2,4-dichlorophenyl 0-ethylphenylphosphonothioate), methyl-parathion, oxydemeton-methyl, ethion, dioxabezofos, cyanophos (cyanofos), isoxathion, pyridafenthion, phosalone, metidation, sulprophos (sulprofos), chlorfenvinphos, tetrachlorvinphos, dimethylvinphos, propahos, isofenphos, disulfoton, profenofos, pyraclofos, monocrotophos, azinphos-methyl, aldikarb, methomyl, thiodicarb, carbofuran, carbosulfan, benfuracarb, furathiocarb, propoxur, fenobcarb, metolcarb, isoprocarb, carbaryl (carbaril), pirimicarb, ethiofencarb, dichlophenthion, pirimiphos-methyl, quinalphos, chlorpyriphos-methyl, prothiophos, naled, bendiocarb, oxamyl, alanycarb, chlorethoxyfos, etc.

Pyrethroid insecticides: permethrin, cypermethrin, deltamethrin, fenvalerate, fenpropathrin, piretrine, allethrin, tetramethrin, resmethrin, dimethrin, proparthrin, phenothrin, prothrin, fluvalinate, cyfluthrin, cyhalothrin, flucythrinate, etofenprox, cycloprothrin, tralomethrin, silafluofen, tefluthrin, bifenthrin, acrinathrin, etc.

Acylurea type and other insecticides: diflubenzuron, chlorfluazuron, hexaflumuron, triflumuron, teflubenzuron, flufenoksuron, flucycloxuron, buprofezin, pyriproxyfen, lufenuron, cyromazine, methoprene, endosulphan, diafenthiuron, imidacloprid, fipronil, nicotin-sulfate, rotenone, metaldehyde, machine oil, fenoxycarb, cartap, thiocyclam, bensultap, tebufenozide, chlorphenapyr, emamectin-benzoate, acetamiprid, nitenpyram, pymetrozine, sodium oleate, rapeseed oil, etc.

Nematicides: phenamiphos, fosthiazate, ethoprophos, methyl isothiocyanate, 1,3-dichloropropene, DCIP, etc.

Acaricides: chlororbenzilate, phenisobromolate, dicofol, amitraz, propargit, benzomate, hexythiazox, fenbutatin oxide, polynactins, quinomethionate, chlorfenson, tetradifon, avermectin, milbemectin, clofentezine, pyridaben, fenpyroximate, tebufenpyrad, pyrimidifen, fenothiocarb, dienochlor, etoxazole, halfenprox, etc.

Fungicides: thiophanate-methyl, benomil, carbendazol, thiabendazol, folpet, TMTM, ziram, zineb, maneb, manzeb, polycarbamate, iprobenfos, edifenphos, fthalide, probenazole, isoprothiolane, chlorothalonil, captan, polyoxin, blasticidin-S, kasugamycin, streptomycin, validamycin, tricyclazole, pyroquilone, phenazine oxide, mepronil, flutolanil, pencycuron, iprodione, hymexazol, metalaxyl, triflumizole, triforine, triadimefone, bitertanol, fenarimol, propiconazol, cymoxanil, prochloraz, pefurazoate, hexaconazole, myclobutanil, diclomezine, tecloftalam, propineb, dithianon, fosetyl, vinclozolin, procymidone, oxadixyl, guazatine, propamocarb-hydrochloride, fluazinam, oxolinic acid, hydroxyisoxazole, mepanipyrim.

The compounds of the present invention exhibit excellent pesticidal activities against a wide range of pests such as hemipteran insects, lepidopteran insects, coleopteran insects, dipteran insects, hymenopteran insects, orthopteran insects, isopteran insects, thysanopteran insects, mites and plant-parastic nematodes, and they are able to control pests which have acquired resistance to conventional pesticides. Further, the compounds of the present invention are able to control plant pathogens such as rice blast fungus (*Pyricularia oryzae*), wheat powdery mildew fungus (*Erysiphe graminis*), leaf rust fungus (*Puccinia recondita*), cucumber downy mildew fungus (*Pseudoperonospora cubensis*) and apple scrab fungus (*Venturia inaequalis*). Furthermore, the compounds of the present invention present no substantial acute toxity to mammals, and they are relatively readily hydrolyzable or photodecomposable.

Likewise, pesticides containing the compounds of the present invention as active ingredients exhibit excellent pesticidal activities against a wide range of pests such as hemipteran insects, lepidopteran insects, coleopteran insects, dipteran insects, hymenopteran insects, orthopteran insects, isopteran insects, thysanopteran insects, mites and plant-parastic nematodes. Further, the pesticides of the present invention exhibit excellent fungicidal activities against plant pathogens such as rice blast fungus (*Pyricularia oryzae*), wheat powdery mildew fungus (*Erysiphe graminis*), leaf rust fungus (*Puccinia recondita*), cucumber downy mildew fungus (*Pseudoperonospora cubensis*) and apple scrab fungus (*Venturia inaequalis*).

The following pests and plant pathogenic fungi may be mentioned as such pests and plant pathogens.

Hemipteran insects: bugs (HETEROPTERA) such as bean bug (*Riptortus clavatus*), southern green stink bug (*Nezara viridula*), lygus bugs (Lygus sp.), hairy chinch bug (*Blissus leucopterus*) and pear lace bug (*Stephanitis nashi*); leafhoppers (Circulifer sp.) such as green rice leafhopper (*Nephotettix cincticeps*) and leafhoppers (Empoasca sp., Erythroneura sp., Circulifer sp.); planthoppers (Delphacidae) such as brown rice planthopper (*Nilaparvata lugens*), whitebacked planthopper (*Sogatella furcifera*) and small brown planthopper (*Laodelphax striatellus*); jumping plantlice (Psyllidae) such as Psyllids (Psylla sp.); whiteflies (Aleyrodidae) such as sweetpotato whitefly (*Bemisia tabaci*) and greenhouse whitefly (*Trialeurodes vaporariorum*); aphides (Aphiclidae) such as grapeleaf louse (*Viteus vitifolii*), green peach aphid (*Myzus persicae*), green apple aphid (*Aphis pomi*), cotton aphid (*Aphis gossypii*), *Aphis fabae*, turnip aphid (*Rhopalosiphum psedobrassicas*), glasshouse-potato aphid (*Aulacorthum solani*) and greenbug (*Schizaphis graminum*); mealy bugs or scales such as comstock mealybug (*Pseudococcus comstocki*), red wax scale (*Ceroplastes rubens*), San Jose scale (*Comstockaspis perniciosa*) and arrowhead scale (*Unaspis yanonensis*).

Lepidopteran insects: tortricids (Tortricidae) such as oriental tea tortrix (*Homona magnanima*), summer fruit tortrix (*Adoxophyes orana*), torticids (*Sparganothis pilleriana*), oriental fruit moth (*Grapholitha molesta*), soybean pod borer (*Leguminivora glycinivorella*), codling moth (*Laspeyresia pomonella*), tortricids (Eucosma sp.) and grape berry moth (*Lobesia botrana*); Cochylidae such as grape cochylid (*Eupoecillia ambiquella*); bagworm moths (Psychidae) such as Bambalina sp.; tineids (Tineidae) such as European grain moth (*Nemapogon granellus*) and casemaking clothes moth (*Tinea translucens*); lyonetiid moths (Lyonetiidae) such as *Lyonetia prunifoliella*; leafblotch miners such as apple leafminer (*Phyllonorycter rigoniella*); Phyllocnistidae such as citrus leafminer (*Phyllocnistis citrella*); yponomeutids such as diamondback moth (*Plutella xylostella*) and yponomeutid moths (*Prays citri*); clearwing moths (Synanthedon sp.) such as grape clearwing moth (*Paranthrene regalis*) and Synanthedon sp.; gelechiid moths (Gelechiidae) such as pink bollworm (*Pectinophora gossypiella*), potato tuberworm (*Phthorimaea operculella*) and Stomopteryx sp.; Carposinidae such as peach fruit moth (*Carposina niponensis*); slug caterpillarmoths such as oriental moth (*Monema flavescens*); pyralid moths such as rice stem borer (*Chilo suppressalis*), rice leafroller (*Cnaphalocrocis medinalis*), European corn borer (*Ostrinia nubilalis*), oriental corn borer (*Ostrinia furnacalis*), cabbage webworm (*Hellula undalis*), greater wax moth (*Galleria mellonella*), lesser cornstalk borer (*Elasmopalpus lignosellus*) and beet webworm (*Loxostege sticticalis*); whites such as common cabbage worm (*Pieris rapae*); geometrid moths such as mugwort looper (*Ascotis selenaria*); tent caterpillar moths such as tent caterpillar (*Malacosoma neustria*); sphinx moths such as tobacco hornworm (*Manduca sexta*); tussock moths such as tea tussock moth (*Euproctis pseudoconspersa*) and gypsy moth (*Lymantria dispar*); tiger moths such as fall webworm (*Hyphantria cunea*); owlet moths such as tobacco budworm (*Heliothis virescens*), bollworm (*Helicoverpa zea*), beet armyworm (*Spodoptera exigua*), cotton bollworm (*Helicoverpa armigera*), common cutworm (*Spodoptera litura*), cabbage armyworm (*Mamestra brassicae*), black cutworm (*Agrotis ipsiron*), rice armyworm (*Pseudaletia separata*) and cabbage looper (*Trichoplusia ni*).

Coleopteran insects: chafers such as cupreous chafer (*Anomala cuprea*), Japanese beetle (*Popillia japonica*), soybean beetle (*Anomala rufocuprea*) and *Eutheola rugiceps*; click beetles (Conodeus sp.) such as wireworm (Agriotes sp.) and Conodeus sp.; ladybird beetles such as twenty-eight-spotted ladybird (*Epilachna vigintioctopunctata*) and Mexican bean beetle (*Epilachna varivestis*); darkling beetles such as red-brown rice-flour beetle (Tribolium castaneum); longicorn beetles such as whitespotted longicorn beetle (*Anoplophora malasiaca*) and Japanese pine sawyer (*Monochamus alternatus*); seed beetles such as bean weevil (*Acanthoscelides obtectus*) and adzuki bean weevil (*Callosobruchus chinensis*); leaf beetles such as colorado potato beetle (*Leptinotarsa decemlineata*), corn rootworm (Diabrotica sp.), rice leaf beetle (*Oulema oryzae*), beet flea beetle (*Chaetocnema concinna*), mustard beetle (*Phaedon cochlearias*), cereal leaf beetle (*Oulema melanopus*) and *Dicladispa armigera*; Apionidae such as *Apion godmani*; weevils such as rice water weevil (*Lissorhoptrus oryzophilus*) and cotton boll weevil (*Anthonomus grandis*); Rhynchophoridae such as maize weevil (*Sitophilus zeamais*); bark beetles; skin beetles; drugstore beetles.

Dipteran insects: rice crane fly (*Tipra ano*), rice midge (*Tanytarsus oryzae*), *Orseolia oryzae*, *Ceratitis capitata*, rice leafminer (*Hydrellia griseola*), cherry drosophila (*Drosophila suzukii*), frit fly (*Oscinella frit*), rice stem maggot (*Chlorops oryzae*), French bean miner (*Ophiomyia phaseoli*), legume leafminer (*Liriomyza trifolii*), beet leafminer (*Pegomya hyoscyami*), seedcorn maggot (*Hylemia platura*), sorghum fly (*Atherigona soccata*), muscid fly (*Musca domestica*), Gastrophilus sp., stomoxiid flies (Stomoxys sp.), *Aedes aegypti*, *Culex pipiens*, *Anopheles sinensis* and *Culex tritaeniorhynchus*.

Hymenopteran insects: stem sawflies (Cephus sp.); eurytomids (Harmolita sp.); cabbage sawfly (Athalia sp.), hornets (Vespa sp.) and fire ants.

Orthopteran insects: German cockroach (*Blatella germanica*); American cockroach (*Periplaneta americana*); mole crichet (*Gryllotalpa africana*); Asiatic locust (*Locusta migratoria migratoriodes*); and *Melanoplus sanguinipes*.

Termites insects: termites (*Reticulitermes speratus*) and formosan subterranean termite (*Coptotermes formosanus*).

Thrips insects: yellow tea thrips (*Scirtothrips dorsalis*); thrips (*Thrips palmi*); greenhouse thrips (*Heliothrips haemorrholidalis*); western flower thrips (*Frankliniella occidentalis*) and rice aculeated thrips (*Haplothrips aculeatus*).

Mites: twospotted spider mite (*Tetranychus urticae*); Kanzawa spider mite (*Tetranychus kanzawai*); citrus red mite (*Panonychus citri*); European red mite (*Panonychus ulmi*), yellow spider mite (*Eotetranychus carpini*); Texas citrus mite (*Eotetranychus banksi*); citrus rust mite (*Phyllocoptruta oleivora*); broad mite (*Polyphagotarsonemus latus*); false spider mites (Brevipalpus sp.); bulb mite (*Rhizoglyphus robini*) and mold mite (*Tyrophagus putrescentiae*).

Plant-parasitic nematodes: southern root-knot nematode (*Meloidogyne incognita*); root-lesion nematode (*Pratylenchus* sp.); soybean cyst nematode (*Heterodera glycines*); rice white-tip nematode (*Aphelenchoides besseyi*) and pine wood nematode (*Bursaphelenchus xylophilus*).

Other pests and parasites: Gastropoda such as apple snails (*Pomacea canaliculata*); slugs (Incilaria sp.) and giant African snail (*Achatina fulica*); pillbugs (Isopoda) such as sow bug and centipede; booklice (Liposcelis sp.); oriental siverfish (Ctenolepisma sp.); Pulex sp.; Trichodectes sp.; Cimex sp.; aminal-parasitic mites such as *Booplilus microplus* and *aemaphysalis longicornis* and Epidermoptidae.

Further, the compounds of the present invention are effective also against pests which show resistance to organophosphorus compounds, carbamate compounds, synthetic pyrethroid compounds, acylurea compounds or conventional insecticides.

Furthermore, the compounds of the present invention are able to control plant diseases caused by plant pathogenic fungi belonging to Oomycetes, Ascomycetes, Deuteromycetes and Basidiomycetes. The following specific fungi may be mentioned as non-restrictive examples.

Genus Pseudoperonospora such as downy mildew fungus (*Pseudoperonospora cubensis*); Genus Sphaerotheca such as powdery mildew fungus (*Sphaerotheca fuliginea*); Genus Erysiphe such as wheat powdery mildew fungus (*Erysiphe graminis*); Genus Venturia such as apple scab fungus (*Venturia inaequalis*); Genus Piricularia such as blast fungus (*Pyricularia oryzae*); Genus Gibberella such as 'Bakanae' disease fungus (*Gibberella fujikuroi*); Genus Botrytis such as gray mold fungus (*Botrytis cinerea*); Genus Alternaria such as Alternaria sooty spot fungus (*Alternaria brassicicola*); Genus Rhizoctoni such as sheath blight fungus (*Rhizoctonia solani*); and Genus Puccinia such as wheat leaf rust fungus (*Puccinia recondita*).

Now, formulation methods will be described in detail with reference to typical Formulation Examples. However, it should be understood that the types and the proportions of the compounds and the adjuvants are not restricted by these specific Examples and may be varied within wide ranges. In the following examples, "%" means "% by weight".

FORMULATION EXAMPLE 1
Emulsifiable concentrate

30% of compound (II-54), 20% of cyclohaxanone, 11% of polyoxyethylene alkylaryl ether, 4% of calcium alkylbenzene sulfonate and 35% of methylnaphthalene were uniformly dissolved to obtain an emulsifiable concentrate.

FORMULATION EXAMPLE 2
Wettable powder

10% of compound (II-54), 0.5% of a sodium salt of a naphthalene sulfonic acid/formalin condensation product, 0.5%, of polyoxyethylene alkylaryl ether, 24% of diatomaceous earth and 65% of clay were uniformly mixed and pulverized to obtain a wettable powder.

FORMULATION EXAMPLE 3
Dust

2% of compound (II-54), 5% of diatomaceous earth and 93% of clay were uniformly mixed and pulverized to obtain a dust.

FORMULATION EXAMPLE 3
Granule

5% of compound (II-54), 2% of sodium lauryl alcohol sulfate, 5% of sodium lignin sulfonate, 2% of carboxymethylcellulose and 86% of clay were uniformly mixed and pulverized. 100 parts by weight of this mixture was kneaded with 20 parts by weight of water and formed into granules of from 14 to 32 mesh by an extrusion-type granulator, followed by drying to obtain a granule formulation.

Now, the effects of the pesticides containing the compounds of the present invention as active ingredients will be described with reference to Test Examples.

Test Example 1

Insecticidal test for beet armyworm

The wettable powder prepared according to Formulation Example 2 was diluted with water so that the concentration of the active ingredient was 500 ppm. Cabbage leaves were immersed in the resulting diluted solution, dried in air and then placed in a polyvinyl chloride cup. Ten larvae of beet armyworm (*Spodoptera exigua*) were released in the cup, and thereafter a cover was placed thereon. Then, the cup was placed in a thermostatic chamber of 25° C for 6 days, and the number of insects died was counted to calculate the mortality (%) according to a calculation formula (A). The results are shown in Tables 21 to 24. The test was carried out in one series.

$$\text{Mortality } (\%) = \frac{\text{Number of insects died}}{\text{Number of insects released}} \times 100 \quad (A)$$

TABLE 21

| Compound No. | Mortality |
| --- | --- |
| I-15 | 100 |
| I-16 | 100 |
| I-39 | 10 |
| I-41 | 100 |
| I-43 | 100 |
| I-45 | 100 |
| I-47 | 100 |
| I-49 | 100 |
| I-51 | 100 |
| I-53 | 100 |
| I-55 | 100 |
| I-57 | 100 |
| I-59 | 100 |
| I-63 | 100 |
| I-69 | 100 |
| I-71 | 100 |
| I-81 | 100 |
| I-83 | 100 |
| I-93 | 100 |
| I-95 | 100 |
| I-96 | 100 |
| I-97 | 100 |
| I-99 | 100 |
| I-101 | 100 |
| I-103 | 100 |
| I-114 | 100 |
| I-115 | 100 |
| I-116 | 100 |
| I-117 | 100 |
| I-118 | 100 |

TABLE 22

| Compound No. | Mortality |
|---|---|
| I-129 | 100 |
| II-39 | 100 |
| II-40 | 100 |
| II-41 | 100 |
| II-42 | 100 |
| II-43 | 100 |
| II-44 | 100 |
| II-46 | 100 |
| II-48 | 100 |
| II-50 | 100 |
| II-52 | 100 |
| II-53 | 100 |
| II-54 | 100 |
| II-55 | 100 |
| II-56 | 100 |
| II-57 | 100 |
| II-58 | 100 |
| II-59 | 100 |
| II-60 | 100 |
| II-64 | 100 |
| II-68 | 100 |
| II-70 | 100 |
| II-72 | 100 |
| II-81 | 100 |
| II-82 | 100 |
| II-83 | 100 |
| II-84 | 100 |
| II-95 | 100 |
| II-96 | 100 |
| II-114 | 100 |

TABLE 23

| Compound No. | Mortality |
|---|---|
| II-116 | 100 |
| II-117 | 100 |
| II-118 | 100 |
| II-126 | 100 |
| II-152 | 100 |
| II-153 | 100 |
| II-154 | 100 |
| II-155 | 100 |
| II-156 | 100 |
| II-157 | 100 |
| II-158 | 100 |
| II-160 | 90 |
| II-161 | 100 |
| II-162 | 100 |
| II-163 | 100 |
| II-164 | 100 |
| II-165 | 100 |
| II-166 | 100 |
| II-167 | 100 |
| II-168 | 100 |
| II-169 | 100 |
| II-170 | 100 |
| II-171 | 100 |
| II-172 | 100 |
| II-173 | 100 |
| II-174 | 100 |
| II-175 | 100 |
| II-176 | 100 |
| II-177 | 100 |
| II-178 | 100 |

TABLE 24

| Compound No. | Mortality |
|---|---|
| II-179 | 100 |
| II-180 | 100 |
| II-181 | 100 |
| II-182 | 100 |
| II-183 | 100 |
| II-184 | 100 |
| II-185 | 100 |
| II-186 | 100 |
| II-187 | 100 |
| II-188 | 100 |
| II-189 | 100 |
| II-190 | 100 |
| II-191 | 100 |
| II-192 | 100 |

Test Example 2

Insecticidal test for cotton aphid

The wettable powder prepared according to Formulation Example 2 was diluted with water so that the concentration of the active ingredient was 100 ppm. Cucumber seedlings which were beforehand inoculated with adults of cotton aphid (*Aphis gossipii*), were immersed in the diluted solution and then dried in air. The cucumber seedlings thus treated, were placed in a thermostatic chamber of 25° C. for 3 days, and then the number of insects died were counted to calculate the mortality (%) according to the following calculation formula (A). The results are shown in Tables 25 to 28. The test was carried out in two series.

TABLE 25

| Compound No. | Mortality |
|---|---|
| I-15 | 100 |
| I-16 | 76 |
| I-39 | 100 |
| I-41 | 100 |
| I-43 | 100 |
| I-45 | 100 |
| I-47 | 100 |
| I-49 | 96 |
| I-51 | 100 |
| I-53 | 96 |
| I-55 | 100 |
| I-57 | 100 |
| I-59 | 100 |
| I-63 | 100 |
| I-71 | 83 |
| I-81 | 100 |
| I-83 | 100 |
| I-93 | 100 |
| I-95 | 100 |
| I-96 | 100 |
| I-97 | 100 |
| I-99 | 91 |
| I-101 | 100 |
| I-103 | 100 |
| I-114 | 100 |
| I-115 | 100 |
| I-116 | 100 |
| I-117 | 100 |
| I-118 | 100 |
| I-129 | 100 |

TABLE 26

| Compound No. | Mortality |
| --- | --- |
| II-39 | 100 |
| II-40 | 100 |
| II-41 | 100 |
| II-42 | 100 |
| II-43 | 100 |
| II-44 | 100 |
| II-46 | 100 |
| II-48 | 100 |
| II-50 | 100 |
| II-52 | 79 |
| II-53 | 100 |
| II-54 | 100 |
| II-55 | 100 |
| II-56 | 95 |
| II-57 | 100 |
| II-58 | 100 |
| II-59 | 100 |
| II-60 | 100 |
| II-64 | 100 |
| II-70 | 100 |
| II-72 | 91 |
| II-81 | 100 |
| II-82 | 100 |
| II-83 | 100 |
| II-84 | 95 |
| II-95 | 100 |
| II-96 | 100 |
| II-114 | 100 |
| II-116 | 100 |
| II-117 | 100 |

TABLE 27

| Compound No. | Mortality |
| --- | --- |
| II-118 | 100 |
| II-126 | 100 |
| II-152 | 100 |
| II-153 | 100 |
| II-154 | 100 |
| II-155 | 100 |
| II-156 | 88 |
| II-157 | 100 |
| II-158 | 100 |
| II-159 | 89 |
| II-161 | 100 |
| II-162 | 100 |
| II-163 | 100 |
| II-164 | 100 |
| II-165 | 100 |
| II-166 | 100 |
| II-167 | 100 |
| II-168 | 100 |
| II-169 | 100 |
| II-170 | 100 |
| II-171 | 100 |
| II-172 | 93 |
| II-173 | 100 |
| II-174 | 100 |
| II-175 | 100 |
| II-176 | 100 |
| II-177 | 100 |
| II-178 | 100 |
| II-179 | 100 |
| II-180 | 100 |

TABLE 28

| Compound No. | Mortality |
| --- | --- |
| II-181 | 100 |
| II-182 | 100 |
| II-183 | 100 |
| II-184 | 100 |
| II-185 | 100 |
| II-186 | 100 |
| II-187 | 100 |
| II-188 | 100 |
| II-189 | 100 |
| II-190 | 100 |
| II-191 | 100 |
| II-192 | 100 |

Test Example 3

Insecticidal test for two-spotted spider mite

The wettable powder prepared according to Formulation Example 2 was diluted with water so that the concentration of the active ingredient was 500 ppm. Soybean seedlings which were beforehand inoculated with adults of two-spotted spider mite (*Tetranychus urticae*), were immersed in the diluted solution and then dried in air. The soybean seedlings thus treated, were placed in a thermostatic chamber of 25° C. for 14 days, and then the number of alive adults were counted to calculate the protective value (%) according to the following calculation formula (B). The results are shown in Tables 29 to 31. The test was carried out in two series.

$$\text{Protective value (\%)} = \left( 1 - \frac{\text{Number of adults before treatment in non-treated area}}{\text{Number of adults before treatment in treated area}} \times \frac{\text{Number of alive adults in treated area}}{\text{Number of alive adults in non-treated area}} \right) \times 100 \quad (B)$$

TABLE 29

| Compound No. | Protective value |
| --- | --- |
| I-39 | 100 |
| I-41 | 100 |
| I-45 | 100 |
| I-47 | 99 |
| I-49 | 100 |
| I-51 | 100 |
| I-53 | 100 |
| I-55 | 100 |
| I-57 | 100 |
| I-59 | 98 |
| I-63 | 100 |
| I-81 | 100 |
| I-83 | 95 |
| I-93 | 100 |
| I-95 | 100 |
| I-96 | 97 |
| I-97 | 100 |
| I-101 | 100 |
| I-103 | 100 |
| I-115 | 99 |
| I-116 | 100 |
| I-118 | 100 |
| II-39 | 97 |
| II-40 | 100 |
| II-41 | 100 |
| II-42 | 100 |
| II-43 | 100 |
| II-44 | 100 |

TABLE 29-continued

| Compound No. | Protective value |
| --- | --- |
| II-46 | 100 |
| II-48 | 100 |

TABLE 30

| Compound No. | Protective value |
| --- | --- |
| II-52 | 100 |
| II-53 | 100 |
| II-54 | 100 |
| II-55 | 100 |
| II-56 | 100 |
| II-57 | 100 |
| II-58 | 100 |
| II-59 | 100 |
| II-60 | 100 |
| II-68 | 99 |
| II-81 | 100 |
| II-83 | 97 |
| II-84 | 97 |
| II-95 | 100 |
| II-96 | 99 |
| II-114 | 100 |
| II-116 | 100 |
| II-117 | 100 |
| II-118 | 100 |
| II-126 | 100 |
| II-152 | 100 |
| II-153 | 100 |
| II-154 | 100 |
| II-157 | 100 |
| II-158 | 100 |
| II-161 | 100 |
| II-162 | 100 |
| II-163 | 100 |
| II-164 | 100 |
| II-165 | 99 |

TABLE 31

| Compound No. | Protective value |
| --- | --- |
| II-166 | 100 |
| II-167 | 100 |
| II-168 | 99 |
| II-169 | 98 |
| II-170 | 100 |
| II-171 | 100 |
| II-172 | 100 |
| II-173 | 100 |
| II-174 | 100 |
| II-176 | 100 |
| II-177 | 100 |
| II-178 | 100 |
| II-182 | 100 |
| II-185 | 97 |
| II-186 | 100 |
| II-187 | 100 |
| II-189 | 100 |
| II-190 | 100 |
| II-191 | 100 |
| II-192 | 100 |

Test Example 4
Test for preventive effects against cucumber downy mildew

Twelve seeds of cucumber (variety: Sagamihanjiro) were sown in each polyvinyl chloride pot of 9 cm×9 cm and cultured in a green house for 7 days. The wettable powder prepared according to Formulation Example 2 was diluted with water so that the concentration of the active ingredient was 500 ppm, and the diluted solution was sprayed to young seedlings of cucumber with developed cotyledons in an amount of 10 ml per pot. After drying the seedlings in air, a suspension of zoosporangium of cucumber downy mildew fungus (*Pseudoperonospora cubensis*) was sprayed and inoculated thereto, and the inoculated seedlings were immediately placed in a humidified chamber at 22° C. for 24 hours. Thereafter, they were transferred to a green house, and after 7 days from inoculation, the presence or absence of the symptoms of a disease of each cotyledons was inspected, whereupon the diseased rate (%) was obtained by the following calculation formula (C), and the protective value (%) was further calculated according to the calculation formula (D). The results are shown in Tables 32 to 34.

$$\text{Diseased rate (\%)} = \frac{\text{Number of leaves diseased}}{\text{Number of leaves tested}} \times 100 \quad \text{(C)}$$

$$\text{Protective value (\%)} = \left(1 - \frac{\text{Number of leaves diseased in treated area}}{\text{Number of leaves diseased in nontreated area}}\right) \times 100 \quad \text{(D)}$$

TABLE 32

| Compound No. | Protective value |
| --- | --- |
| I-15 | 100 |
| I-39 | 100 |
| I-41 | 100 |
| I-43 | 100 |
| I-45 | 100 |
| I-47 | 100 |
| I-49 | 100 |
| I-51 | 100 |
| I-53 | 100 |
| I-55 | 100 |
| I-57 | 100 |
| I-59 | 100 |
| I-69 | 100 |
| I-71 | 100 |
| I-81 | 100 |
| I-83 | 100 |
| I-93 | 100 |
| I-95 | 100 |
| I-96 | 100 |
| I-97 | 100 |
| I-99 | 100 |
| I-101 | 100 |
| I-103 | 100 |
| I-114 | 100 |
| I-115 | 100 |
| I-118 | 100 |
| II-39 | 100 |
| II-40 | 100 |
| II-41 | 100 |
| II-42 | 100 |

TABLE 33

| Compound No. | Protective value |
| --- | --- |
| II-43 | 100 |
| II-44 | 100 |
| II-46 | 100 |
| II-48 | 100 |
| II-50 | 100 |
| II-54 | 100 |
| II-55 | 100 |
| II-56 | 100 |

TABLE 33-continued

| Compound No. | Protective value |
| --- | --- |
| II-57 | 100 |
| II-59 | 100 |
| II-60 | 100 |
| II-68 | 100 |
| II-70 | 100 |
| II-72 | 100 |
| II-81 | 100 |
| II-83 | 100 |
| II-95 | 100 |
| II-96 | 100 |
| II-114 | 100 |
| II-116 | 100 |
| II-118 | 100 |
| II-152 | 100 |
| II-153 | 100 |
| II-154 | 100 |
| II-155 | 100 |
| II-156 | 100 |
| II-157 | 100 |
| II-158 | 100 |
| II-159 | 100 |
| II-161 | 100 |

TABLE 34

| Compound No. | Protective value |
| --- | --- |
| II-162 | 100 |
| II-163 | 100 |
| II-164 | 100 |
| II-165 | 100 |
| II-166 | 100 |
| II-167 | 100 |
| II-168 | 100 |
| II-169 | 100 |
| II-170 | 100 |
| II-173 | 100 |
| II-174 | 100 |
| II-176 | 100 |
| II-177 | 100 |
| II-178 | 100 |
| II-179 | 100 |
| II-180 | 100 |
| II-181 | 100 |
| II-182 | 100 |
| II-183 | 100 |
| II-184 | 100 |
| II-188 | 100 |

Test Example 5
Test for preventive effects against wheat powdery mildew

Twelve seeds of wheat (variety: Norin No. 61) were sown in each polyvinyl chloride pot of 9 cm×9 cm and cultured in a green house for 10 days. The wettable powder prepared according to Formulation Example 2 was diluted with water so that the concentration of the active ingredient was 50 ppm. and the diluted solution was sprayed to the wheat seedlings in an amount of 10 ml per pot. After drying the seedlings, spores of wheat powdery mildew fungus (Erysiphe graminis) were inoculated thereto, and the seedlings were placed in a green house of from 25° to 30° C. After 10 days from inoculation, the diseased degree of the first leaf was evaluated in accordance with the standards as identified in Table 35, whereupon the damaged rate (%) was calculated by the following calculation formula (E) from the index thereby obtained, and the preventive value (%) was further obtained by the calculation formula (F). The results are shown in Table 36.

TABLE 35

| Diseased index | Diseased area |
| --- | --- |
| 0 | No disease observed |
| 1 | Less than 5% |
| 2 | At least 5% and less than 33.3% |
| 3 | At least 33.3% and less than 66.6% |
| 4 | At least 66.6% |

$$\text{Diseased rate (\%)} = \frac{\Sigma \text{ (index} \times \text{number of relevant leaves)}}{\text{Number of leaves tested} \times 4} \times 100 \quad \text{(E)}$$

$$\text{Preventative value (\%)} = \left(1 - \frac{\text{Damaged rate in treated area}}{\text{Damaged rate in non-treated area}}\right) \times 100 \quad \text{(F)}$$

TABLE 36

| Compound No. | Protective value |
| --- | --- |
| I-51 | 100 |
| I-53 | 100 |
| I-96 | 100 |
| I-97 | 100 |
| II-53 | 100 |
| II-81 | 100 |
| II-95 | 100 |
| II-153 | 100 |
| II-155 | 100 |
| II-162 | 100 |

Test Example 6
Test for preventive effects against apple scab

Five seeds of apple (variety: Kougyoku) were sown in each polyvinyl chloride pot of 9 cm×9 cm and cultured in a green house for 20 days. The wettable powder prepared in accordance with Formulation Example 2 was diluted with water so that the concentration of the active ingredient was 500 ppm. and the diluted solution was sprayed to the seedlings having four developed foliage leaves in an amount of 20 ml per pot. After drying the seedlings in air, a suspension of spores of apple scab fungus (Venturia inaequalis) was sprayed and inoculated thereto, and the seedlings were immediately placed in a humidified chamber at 22° C. for 48 hours. Thereafter, they were transferred to a green house and after 14 days from inoculation, the diseased degree of each foliage leaf was evaluated in accordance with the standards as identified in Table 35. On the basis of the index values thereby obtained, the diseased rate (%) was obtained by the following calculation formula (G), and the preventive value (%) was further calculated according to the calculation formula (H). The results are shown in Table 37.

$$\text{Diseased rate (\%)} = \frac{\Sigma \text{ (index} \times \text{number of relevant leaves)}}{\text{Number of leaves tested} \times 4} \times 100 \quad \text{(G)}$$

$$\text{Preventative value (\%)} = \left(1 - \frac{\text{Damaged rate in treated area}}{\text{Damaged rate in non-treated area}}\right) \times 100 \quad \text{(H)}$$

TABLE 37

| Compound No. | Protective value |
|---|---|
| I-53 | 100 |

Test Example 7

Test for preventive effects against wheat leaf rust

Twelve seeds of wheat (variety: Norin No. 61) were sown in each vinyl chloride pot of 9 cm×9 cm and cultured for ten days in a green house. The wettable powder prepared according to Formulation Example 2 was diluted with water so that the concentration of the active ingredient was 50 ppm, and the diluted solution was sprayed to the wheat in an amount of 10 ml per pot. After drying the wheat in air, a suspension of pores of wheat leaf rust fungus (*Puccinia recondita*) was sprayed and inoculated thereto, and the pot was immediately placed in a humidified chamber at 22° C. for 24 hours. Thereafter, the pot was transferred to a green house of from 25° to 30° C., and after 10 days from inoculation, the number of lesions on the first leaf was counted, and the preventive value (%) was calculated according to the following calculation formula (I). The results are shown in Table 38.

$$\text{Preventative value (\%)} = \left(1 - \frac{\text{Number of lesions in treated area}}{\text{Number of leasions in non-treated area}}\right) \times 100$$

TABLE 38

| Compound No. | Protective value |
|---|---|
| I-95 | 100 |
| I-97 | 100 |
| II-153 | 100 |

Test Example 8

Acute toxity against mice by oral administration

A test compound was suspended in a 0.5% carboxymethylcellulose solution having Tween 80 added or in corn oil, depending upon its physical properties, and the suspension was forcibly orally administered to ddy male mice of 8 weeks old by means of a metal sonde. The dose was 30 mg/kg, and 0.1 ml per 10 g of the body weight was administered. A group of three mice was used for each test. Everyday for seven days after administration, the presence or absence of toxic symptoms and death was inspected. The results are shown in Table 39.

The Comparative Compounds employed are as follows.

Compound A: N-(3-chloro-2-ethylpyridin-4-yl)-4-(4-chlorophenoxy)phenylacetamide (Compound No. 30 as disclosed in Japanese Unexamined Patent Publication No. 221990/1993).

Compound B: N-(3-chloro-2-ethylpyridin-4-yl)-4-(4-cyanophenoxy)phenylacetamide (Compound No. 36 as disclosed in Japanese Unexamined Patent Publication No. 221990/1993).

TABLE 39

| Compound No. | Mortality (%) |
|---|---|
| I-118 | 0 |
| II-44 | 0 |
| II-54 | 0 |
| II-116 | 0 |
| A | 100 |
| B | 100 |

We claim:

1. A pyridine compound of the formula (I), or its oxide or salt:

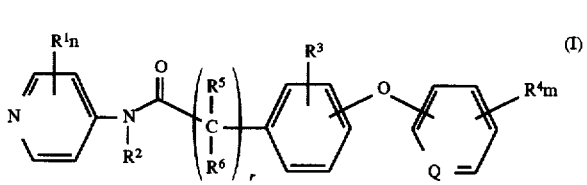

(I)

wherein $R^1$ is a halogen atom, a $C_{1-6}$ alkyl group, a $Cl_{1-6}$ haloalkyl group, a $C_{3-7}$ cycloalkyl group, a $C_{1-6}$ alkoxy group or a $C_{1-6}$ haloalkoxy group, provided that a plurality of $R^1$ may be the same or different; $R^2$ is a $C_{2-6}$ alkenyl group, a $C_{2-6}$ alkynyl group, an alkoxyalkyl group, an alkoxycarbonylalkyl group, a group of the formula —COOR$^7$ (wherein $R^7$ is a $C_{1-10}$ alkyl group, a $C_{1-10}$ haloalkyl group, a $C_{2-6}$ alkenyl group, a $C_{2-6}$ alkynyl group, a $C_{3-7}$ cycloalkyl group, a cycloalkylalkyl group, an alkoxyalkyl group, a phenyl group (which may be substituted by a halogen atom, a nitro group, a $C_{1-6}$ alkyl group, a $C_{1-6}$ haloalkyl group or a $C_{1-6}$ alkoxy group), or a benzyl group (which may be substituted by a halogen atom, a nitro group, a $C_{1-6}$ alkyl group, a $C_{1-6}$ haloalkyl group or a $C_{1-6}$ alkoxy group)) or a group of the formula —SNR$^9$R$^{10}$ (wherein $R^9$ is a $C_{1-6}$ alkyl group, an alkoxycarbonyl group or an alkoxycarbonylalkyl group, and $R^{10}$ is a $C_{1-6}$ alkyl group, an alkoxycarbonyl group or an alkoxycarbonylalkyl group, provided that $R^9$ and $R^{10}$ may be the same or different); $R^3$ is a hydrogen atom, a halogen atom, a $C_{1-6}$ alkyl group or a $C_{1-6}$ alkoxy group; $R^4$ is a halogen atom, a cyano group, a nitro group, a $C_{1-6}$ alkyl group, a $C_{1-6}$ haloalkyl group, a group of the formula —COOR$^8$ (wherein $R^8$ is a $C_{1-6}$ alkyl group, a benzyl group or an alkyl-substituted silylalkyl group), a $C_{1-6}$ alkylthio group, a $C_{1-6}$ alkylsulfinyl group, a $C_{1-6}$ alkylsulfonyl group, a $C_{1-6}$ haloalkoxy group or a $C_{1-6}$ haloalkylthio group, provided that a plurality of $R^4$ may be the same or different; each of $R^5$ and $R^6$ which may be the same or different, is a hydrogen atom or a $C_{1-6}$ alkyl group; Q is a methine group or a nitrogen atom; m is an integer of from 0 to 2; n is an integer of from 0 to 4; and r is an integer of from 1 to 4.

2. The compound according to claim 1, wherein in the formula (I), R is a chlorine atom and an ethyl group; $R^2$ is an alkoxyalkyl group, an alkoxycarbonyl alkyl group, an alkenyl group, an alkynyl group, an alkoxycarbonyl group, an alkenyloxycarbonyl group, an alkynyloxycarbonyl group, a benzyloxycarbonyl group or a 4-chlorobenzyloxycarbonyl group; $R^3$ is a hydrogen atom, a fluorine atom or a chlorine atom; $R^4$ is a chlorine atom, a bromine atom, a cyano group, a nitro group, a trifluoromethyl group, an alkylthio group, an alkylsulfinyl group, an alkylsulfonyl group, a haloalkoxy group or a haloalkylthio group; each of $R^5$ and $R^6$ is a hydrogen atom; Q is a methine group or a nitrogen atom; m is 1; n is 2; and r is 1.

3. The compound according to claim 1, wherein in the formula (I), $R^1$ is a chlorine atom and an ethyl group; $R^2$ is an alkynyl group, an alkoxycarbonyl group, an alkenyloxycarbonyl group, an alkynyloxycarbonyl group, a benzyloxycarbonyl group or a 4-chlorobenzyloxycarbonyl group; $R^3$ is a hydrogen atom, a fluorine atom or a chlorine atom; $R^4$ is a chlorine atom, a cyano group, a nitro group, a trifluoromethyl group, a methylthio group, a methylsulfinyl group, a methylsulfonyl group, a trifluoromethoxy group or a trifluoromethylthio group; each of $R^5$ and $R^6$ is a hydrogen atom; Q is a methine group or a nitrogen atom; m is 1; n is 2; and r is 1.

4. The compound according to claim 1, wherein in the formula (I), $R^1$ is a chlorine atom and an ethyl group; $R^2$ is a propargyl group, a methoxycarbonyl group or an allyloxycarbonyl group; $R^3$ is a hydrogen atom; $R^4$ is a chlorine atom, a cyano group, a nitro group or a trifluoromethyl group; each of $R^5$ and $R^6$ is a hydrogen atom; Q is a methine group or a nitrogen atom; m is 1; n is 2; and r is 1.

5. A process for producing a compound according to claim 1 of the formula (I):

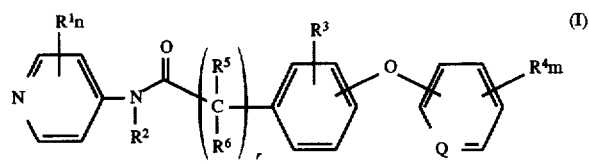

wherein $R^1$, $R^2$, $R^3$, $R^4$, $R^5$, $R^6$, Q, m, n and r are as defined in claim 1, which comprises reacting a compound of the formula (II):

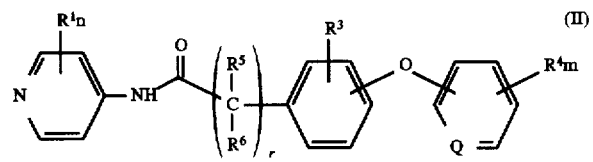

with a compound of the formula $R^2$-X wherein X is a halogen atom, an alkoxycarbonyloxy group, an alkylsulfonyloxy group, a benzenesulfonyloxy group or a toluenesulfonyloxy group, and $R^2$ is as defined in claim 1, in the presence of a base and a solvent.

6. A process for producing a compound according to claim 1 of the formula (I):

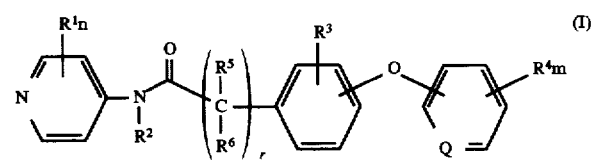

wherein $R^1$, $R^2$, $R^3$, $R^4$, $R^5$, $R^6$, Q, m, n and r are as defined in claim 1, which comprises reacting a compound of the formula (IV):

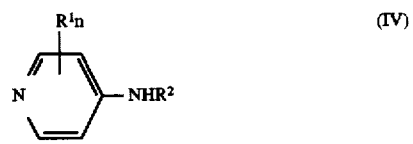

with a compound of the formula (V):

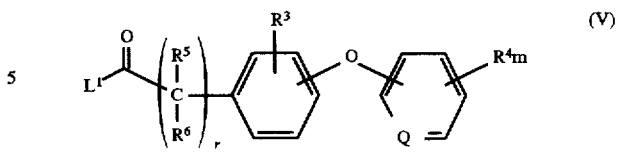

in the presence of a base and a solvent.

7. A pesticide comprising a carrier and an effective amount of a pyridine compound of the formula (I), or its oxide or salt:

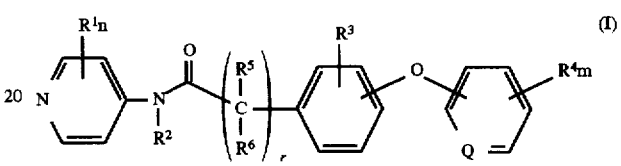

wherein $R^1$ is a halogen atom, a $C_{1-6}$ alkyl group, a $C_{1-6}$ haloalkyl group, a $C_{3-7}$ cycloalkyl group, a $C_{1-6}$ alkoxy group or a $C_{1-6}$ haloalkoxy group, provided that a plurality of $R^1$ may be the same or different; $R^2$ is a $C_{2-6}$ alkenyl group, a $C_{2-6}$ alkynyl group, an alkoxyalkyl group, an alkoxycarbonylalkyl group, a group of the formula —COOR$^7$ (wherein $R^7$ is a $C_{1-10}$ alkyl group, a $C_{1-10}$ haloalkyl group, a $C_{2-6}$ alkenyl group, a $C_{2-6}$ alkynyl group, a $C_{3-7}$ cycloalkyl group, a cycloalkylalkyl group, an alkoxyalkyl group, a phenyl group (which may be substituted by a halogen atom, a nitro group, a $C_{1-6}$ alkyl group, a $C_{1-6}$ haloalkyl group or a $C_{1-6}$ alkoxy group), or a benzyl group (which may be substituted by a halogen atom, a nitro group, a $C_{1-6}$ alkyl group, a $C_{1-6}$ haloalkyl group or a $C_{1-6}$ alkoxy group)) or a group of the formula —SNR$^9$R$^{10}$ (wherein $R^9$ is a $C_{1-6}$ alkyl group, an alkoxycarbonyl group or an alkoxycarbonylalkyl group, and $R^{10}$ is a $C_{1-6}$ alkyl group, an alkoxycarbonyl group or an alkoxycarbonylalkyl group, provided that $R^9$ and $R^{10}$ may be the same or different); $R^3$ is a hydrogen atom, a halogen atom, a $C_{1-6}$ alkyl group or a $C_{1-6}$ alkoxy group; $R^4$ is a halogen atom, a cyano group, a nitro group, a $C_{1-6}$ alkyl group, a $C_{1-6}$ haloalkyl group, a group of the formula —COOR$^8$ (wherein $R^8$ is a $C_{1-6}$ alkyl group, a benzyl group or an alkyl-substituted silylalkyl group), a $C_{1-6}$ alkylthio group, a $C_{1-6}$ alkysulfonyl group, a $C_{1-6}$ alkylsulfonyl group, a $C_{1-6}$ haloalkoxy group or a $C_{1-6}$ haloalkylthio group, provided that a plurality of $R^4$ may be the same or different; each of $R^5$ and $R^6$ which may be the same or different, is a hydrogen atom or a $C_{1-6}$ alkyl group; Q is a methine group or a nitrogen atom; m is an integer of from 0 to 2; n is an integer of from 0 to 4; and r is an integer of from 1 to 4.

* * * * *